(12) United States Patent
Yoshida et al.

(10) Patent No.: US 12,159,719 B2
(45) Date of Patent: Dec. 3, 2024

(54) MEDICAL IMAGE DIAGNOSIS APPARATUS, MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Masashi Yoshida, Nasushiobara (JP); Tomohiro Kawasaki, Otawara (JP); Takeshi Ezumi, Otawara (JP); Tomoki Ooyasu, Sakura (JP); Yunosuke Haru, Otawara (JP); Yasuyuki Miyoshi, Nasushiobara (JP); Yasuhito Nagai, Nasushiobara (JP); Yasunori Ohshima, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 562 days.

(21) Appl. No.: 17/394,753

(22) Filed: Aug. 5, 2021

(65) Prior Publication Data
US 2022/0044811 A1 Feb. 10, 2022

(30) Foreign Application Priority Data
Aug. 7, 2020 (JP) .................................. 2020-135099

(51) Int. Cl.
*G16H 50/20* (2018.01)
*A61B 6/00* (2006.01)
(Continued)

(52) U.S. Cl.
CPC ............. *G16H 50/20* (2018.01); *A61B 6/481* (2013.01); *A61B 34/20* (2016.02); *A61B 34/25* (2016.02);
(Continued)

(58) Field of Classification Search
CPC ........ G16H 50/20; G16H 30/40; G16H 40/63; G16H 20/40; A61B 6/481; A61B 34/20;
(Continued)

(56) References Cited

U.S. PATENT DOCUMENTS 10,070,903 B2 * 9/2018 Blau ....................... A61B 90/11
10,956,492 B2 * 3/2021 Barral .................... G16H 30/40
(Continued)

FOREIGN PATENT DOCUMENTS

CN 112262437 * 1/2021 ............. G16H 10/60
JP 2002-238884 A 8/2002
(Continued)

OTHER PUBLICATIONS

Japanese Office Action issued Dec. 12, 2023 in Japanese Patent Application No. 2020-135099, 2 pages.

*Primary Examiner* — Jerome Grant, II
(74) *Attorney, Agent, or Firm* — Oblon, McClelland, Maier & Neustadt, L.L.P.

(57) ABSTRACT

A medical image diagnosis apparatus for use in a therapeutic procedure to a subject includes processing circuitry. The processing circuitry is configured to determine a status of a current therapeutic procedure; determine at least one proposed preset of settings of the medical image diagnosis apparatus according to the status of the current therapeutic procedure; and perform a control in accordance with the at least one proposed preset.

19 Claims, 9 Drawing Sheets

(51) Int. Cl.
*A61B 34/00* (2016.01)
*A61B 34/20* (2016.01)
*A61B 90/00* (2016.01)
*G06T 7/00* (2017.01)
*G06T 7/70* (2017.01)
*G16H 30/40* (2018.01)
*G16H 40/63* (2018.01)

(52) U.S. Cl.
CPC ............ *A61B 90/37* (2016.02); *G06T 7/0012* (2013.01); *G06T 7/70* (2017.01); *G16H 30/40* (2018.01); *G16H 40/63* (2018.01); *A61B 2034/2065* (2016.02); *G06T 2207/10116* (2013.01); *G06T 2207/10132* (2013.01); *G06T 2207/30021* (2013.01)

(58) Field of Classification Search
CPC . A61B 34/25; A61B 90/37; A61B 2034/2065; A61B 6/032; A61B 6/12; A61B 6/4014; A61B 6/545; A61B 90/36; A61B 2017/00203; A61B 2034/258; A61B 2090/371; A61B 2090/376; A61B 2090/378; A61B 2576/00; G06T 7/0012; G06T 7/70; G06T 2207/10116; G06T 2207/10132; G06T 2207/30021
USPC .......................................................... 366/241
See application file for complete search history.

(56) References Cited

U.S. PATENT DOCUMENTS

| 11,080,424 | B2 * | 8/2021 | Venkataraman | ........ G16H 10/60 |
| 11,751,953 | B2 * | 9/2023 | Patton | ..................... A61F 9/008 |
| | | | | 600/424 |
| 2006/0100738 | A1 | 5/2006 | Alsafadi et al. | |
| 2006/0142745 | A1 | 6/2006 | Boutoussov | |
| 2019/0206562 | A1 * | 7/2019 | Shelton, IV | ............ A61M 1/79 |

FOREIGN PATENT DOCUMENTS

| JP | 2002238884 | * | 8/2002 | |
| JP | 2005-176996 A | | 7/2005 | |
| JP | 2016-106848 A | | 6/2016 | |
| JP | 2019118711 | * | 7/2019 | ............... A61B 6/03 |

* cited by examiner

FIG.2

| No. | USER ID | THERAPEUTIC PROCEDURE | STATUS | PRESET |
|---|---|---|---|---|
| 1 | DEFAULT | CEREBRAL ANEURYSM COIL EMBOLIZATION | START OF CATHETER INSERTION | ·ANGLE IS SET TO BIPLANE REFERENCE POSITION<br>·ADJUST HORIZONTAL CATHETER INSERTION POSITION TO SCREEN CENTER |
| 2 | A0001 | CEREBRAL ANEURYSM COIL EMBOLIZATION | START OF CATHETER INSERTION | ·ADJUST CATHETER INSERTION POSITION TO ONE-THIRD OF THE SCREEN IN THE BOTTOM |
| 3 | DEFAULT | CEREBRAL ANEURYSM COIL EMBOLIZATION | CATHETER IN MOTION | ·BIPLANE REFERENCE POSITION<br>·MOVE FPD TOWARD THE PATIENT AS CLOSE AS POSSIBLE BUT NOT TO CONTACT THE PATIENT |
| 4 | A0001 | CEREBRAL ANEURYSM COIL EMBOLIZATION | CATHETER IN MOTION | ·BIPLANE REFERENCE POSITION |
| 5 | DEFAULT | CEREBRAL ANEURYSM COIL EMBOLIZATION | CATHETER IN MOTION (CATHETER REACHING SCREEN TOP END) | ·MOVE C-ARM IN PARALLEL FOLLOWING MOVING CATHETER |
| 6 | A0001 | CEREBRAL ANEURYSM COIL EMBOLIZATION | CATHETER IN MOTION (CATHETER REACHING SCREEN TOP END) | ·SLIDE COUCH TABLE-TOP FOLLOWING MOVING CATHETER |
| 7 | DEFAULT | CEREBRAL ANEURYSM COIL EMBOLIZATION | CATHETER REACHING THE HEAD | ·SINGLE-PLANE REFERENCE POSITION (MOVE CATHETER INTO THE HEAD) |
| 8 | DEFAULT | CEREBRAL ANEURYSM COIL EMBOLIZATION | COIL PLACEMENT | ·TILT OF C-ARM IS PRESET OR SET TO AUTOMATICALLY SET WORKING ANGLE<br>·ADJUST HORIZONTAL AND VERTICAL MOTION AROUND ANEURYSM |
| 9 | A0001 | CEREBRAL ANEURYSM COIL EMBOLIZATION | COIL PLACEMENT | ·TILT OF C-ARM IS PRESET OR SET TO AUTOMATICALLY SET WORKING ANGLE<br>·OR ADJUSTED TO CENTER OF THE RIGHT OR LEFT BRAIN HAVING ANEURYSM<br>(USE ANATOMICAL LANDMARK) |
| 10 | DEFAULT | CEREBRAL ANEURYSM COIL EMBOLIZATION | STENT PLACEMENT | ·USE STENT ENHANCEMENT APPLICATION |
| ... | ... | ... | ... | ... |

FIG.3

| No | USER ID | THERAPEUTIC PROCEDURE | STATUS | PRESET |
|---|---|---|---|---|
| ... | ... | ... | ... | ... |
| 100 | DEFAULT | CEREBRAL ANEURYSM COIL EMBOLIZATION | CEREBRAL ANEURYSM ANALYSIS | •WITHDRAW MONITOR TO NON-DISTURBING LOCATION TO PREPARE FOR CONTRAST INJECTION |
| 101 | A0001 | CEREBRAL ANEURYSM COIL EMBOLIZATION | CEREBRAL ANEURYSM ANALYSIS | •NOT MOVE MONITOR AT THE TIME OF CONTRAST INJECTION (MAINTAIN MONITOR POSITION) |
| 102 | DEFAULT | CEREBRAL ANEURYSM COIL EMBOLIZATION | GENERATE THREE-DIMENSIONAL IMAGE FOR CEREBRAL ANEURYSM ANALYSIS | •THREE-DIMENSIONAL IMAGE (VOLUME RENDERING IMAGE) •CHANGE MONITOR TO DISPLAY LAYOUT |
| 103 | A0001 | CEREBRAL ANEURYSM COIL EMBOLIZATION | GENERATE THREE-DIMENSIONAL IMAGE FOR CEREBRAL ANEURYSM ANALYSIS | •CHANGE MONITOR TO MPR IMAGE (THREE ORTHOGONAL-PLANE IMAGE) DISPLAY LAYOUT |
| ... | ... | ... | ... | ... |

FIG.4

| No. | USER ID | THERAPEUTIC PROCEDURE | STATUS | PRESET | CORRECTION INFORMATION |
|---|---|---|---|---|---|
| 1 | DEFAULT | CEREBRAL ANEURYSM COIL EMBOLIZATION | START OF CATHETER INSERTION | ·ANGLE IS SET TO BIPLANE REFERENCE POSITION<br>·ADJUST HORIZONTAL CATHETER INSERTION POSITION TO SCREEN CENTER | ·ADJUST CATHETER INSERTION POSITION TO ONE-THIRD OF THE SCREEN IN THE BOTTOM |
| 2 | DEFAULT | CEREBRAL ANEURYSM COIL EMBOLIZATION | CATHETER IN MOTION | ·BIPLANE REFERENCE POSITION | ·MOVE FPD TOWARD THE PATIENT AS CLOSE AS POSSIBLE BUT NOT TO CONTACT THE PATIENT |
| 3 | DEFAULT | CEREBRAL ANEURYSM COIL EMBOLIZATION | CATHETER IN MOTION (CATHETER REACHING SCREEN TOP END) | ·MOVE C-ARM IN PARALLEL FOLLOWING MOVING CATHETER | ... |
| 4 | A0001 | CEREBRAL ANEURYSM COIL EMBOLIZATION | CATHETER IN MOTION (CATHETER REACHING SCREEN TOP END) | ·SLIDE COUCH TABLE-TOP FOLLOWING MOVING CATHETER | ... |
| 5 | DEFAULT | CEREBRAL ANEURYSM COIL EMBOLIZATION | CATHETER REACHING THE HEAD | ·SINGLE-PLANE REFERENCE POSITION (MOVE CATHETER INTO THE HEAD) | ... |
| 6 | A0001 | CEREBRAL ANEURYSM COIL EMBOLIZATION | COIL PLACEMENT | ·TILT OF C-ARM IS PRESET OR SET TO AUTOMATICALLY SET WORKING ANGLE | ·ADJUST HORIZONTAL AND VERTICAL MOTION AROUND ANEURYSM |
| 7 | A0001 | CEREBRAL ANEURYSM COIL EMBOLIZATION | COIL PLACEMENT | ·TILT OF C-ARM IS PRESET OR SET TO AUTOMATICALLY SET WORKING ANGLE | ·ADJUSTED TO CENTER OF THE RIGHT OR LEFT BRAIN HAVING ANEURYSM (USE ANATOMICAL LANDMARK) |
| ... | ... | ... | ... | ... | ... |

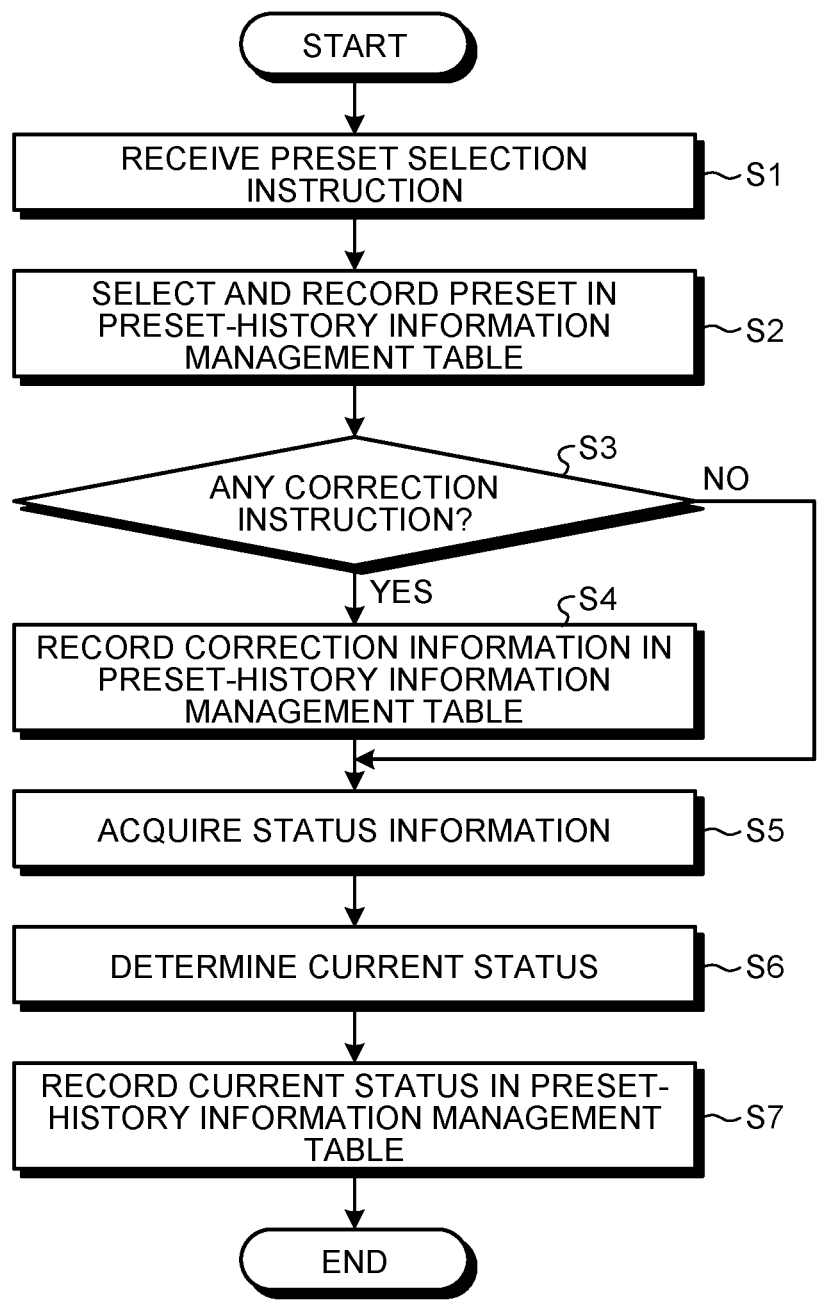

FIG.9

| No. | USER ID | THERAPEUTIC PROCEDURE | STATUS | PRESET |
|---|---|---|---|---|
| 1 | DEFAULT | MITRAL VALVE CLIPPING (MitraClip®) | CLIP APPROACHING THE VALVE | ·MIDESOPHAGUS COMMISSURAL IMAGE (TWO CHAMBER VIEW: 60 TO 90 DEGREES) ·MIDESOPHAGUS AORTIC VALVE LONG AXIS IMAGE (THREE CHAMBER VIEW: 100 TO 160 DEGREES) |
| 2 | ... | ... | ... | ... |
| ... | ... | ... | ... | ... |
| 50 | DEFAULT | MITRAL VALVE CLIPPING (MitraClip®) | CLIP ANGLE ADJUSTMENT | ·3D IMAGE DISPLAY |
| 51 | A0001 | MITRAL VALVE CLIPPING (MitraClip®) | CLIP ANGLE ADJUSTMENT | ·MIDESOPHAGUS COMMISSURAL IMAGE (TWO CHAMBER VIEW: 60 TO 90 DEGREES) ·MIDESOPHAGUS AORTIC VALVE LONG AXIS IMAGE (THREE CHAMBER VIEW: 100 TO 160 DEGREES) |
| ... | ... | ... | ... | ... |
| 100 | DEFAULT | MITRAL VALVE CLIPPING (MitraClip®) | CLIP ATTACHMENT | ·PROPOSE FOR CHANGING ALERT CONDITION TO SET CLIP ATTACHMENT MODE |
| 101 | A0001 | MITRAL VALVE CLIPPING (MitraClip®) | CLIP ATTACHMENT | ·NO CHANGE IN ALERT CONDITION |
| ... | ... | ... | ... | ... |

MEDICAL IMAGE DIAGNOSIS APPARATUS, MEDICAL INFORMATION PROCESSING APPARATUS AND MEDICAL INFORMATION PROCESSING METHOD

CROSS-REFERENCE TO RELATED APPLICATION

This application is based upon and claims the benefit of priority from Japanese Patent Application No. 2020-135099, filed on Aug. 7, 2020; the entire contents of which are incorporated herein by reference.

FIELD

Embodiments described herein relate generally to a medical image diagnosis apparatus, a medical information processing apparatus and a medical information processing method.

BACKGROUND

Interventional radiology (IVR) relies on the use of a medical image diagnosis apparatus (e.g., an X-ray diagnosis apparatus, an ultrasound diagnosis apparatus, an X-ray computer tomography (CT) imaging apparatus, a magnetic resonance imaging (MRI) apparatus), to insert and advance a catheter or a puncture needle into the body to perform treatment to a target region while observing the internal condition of the body in real time with the medical image diagnosis apparatus. The IVR employs a preset function of the medical image diagnosis apparatus. Various settings of the medical image diagnosis apparatus are individually registered as presets. The preset function refers to a function that allows physicians to set the medical image diagnosis apparatus in a desired manner by selecting a desired preset from among the registered presets at desired timing. Examples of the traditional preset function includes adding preset numbers to the individual settings for management purpose, and managing thumb nail images representing details of the individual settings.

Such traditional preset functions have, however, unfavorable features, as follows.

In the case of the preset function to add preset numbers to the individual settings for management purpose, the physician is required to remember the correspondence between the present numbers and the settings. As the number of preset numbers increases, the physician's burden increases. In the case of the preset function to manage thumb nail images representing details of the individual settings, the physician is required to select a preset suitable for a current situation while performing a therapeutic procedure, which is a great burden on the physician.

BRIEF DESCRIPTION OF THE DRAWINGS

FIG. 2 illustrates an exemplary preset-information management table stored in a memory circuit of the X-ray diagnosis apparatus according to an embodiment;

FIG. 3 illustrates another exemplary preset-information management table stored in the memory circuit of the X-ray diagnosis apparatus according to an embodiment;

FIG. 4 illustrates an exemplary preset-history information management table stored in the memory circuit of the X-ray diagnosis apparatus according to an embodiment;

FIG. 5 is a flowchart illustrating a preset-history information generation process to be executed by the X-ray diagnosis apparatus in an embodiment;

FIG. 9 illustrates an exemplary preset-information management table stored in a memory circuit of the ultrasound diagnosis apparatus according to an embodiment.

DETAILED DESCRIPTION

Figure 1:
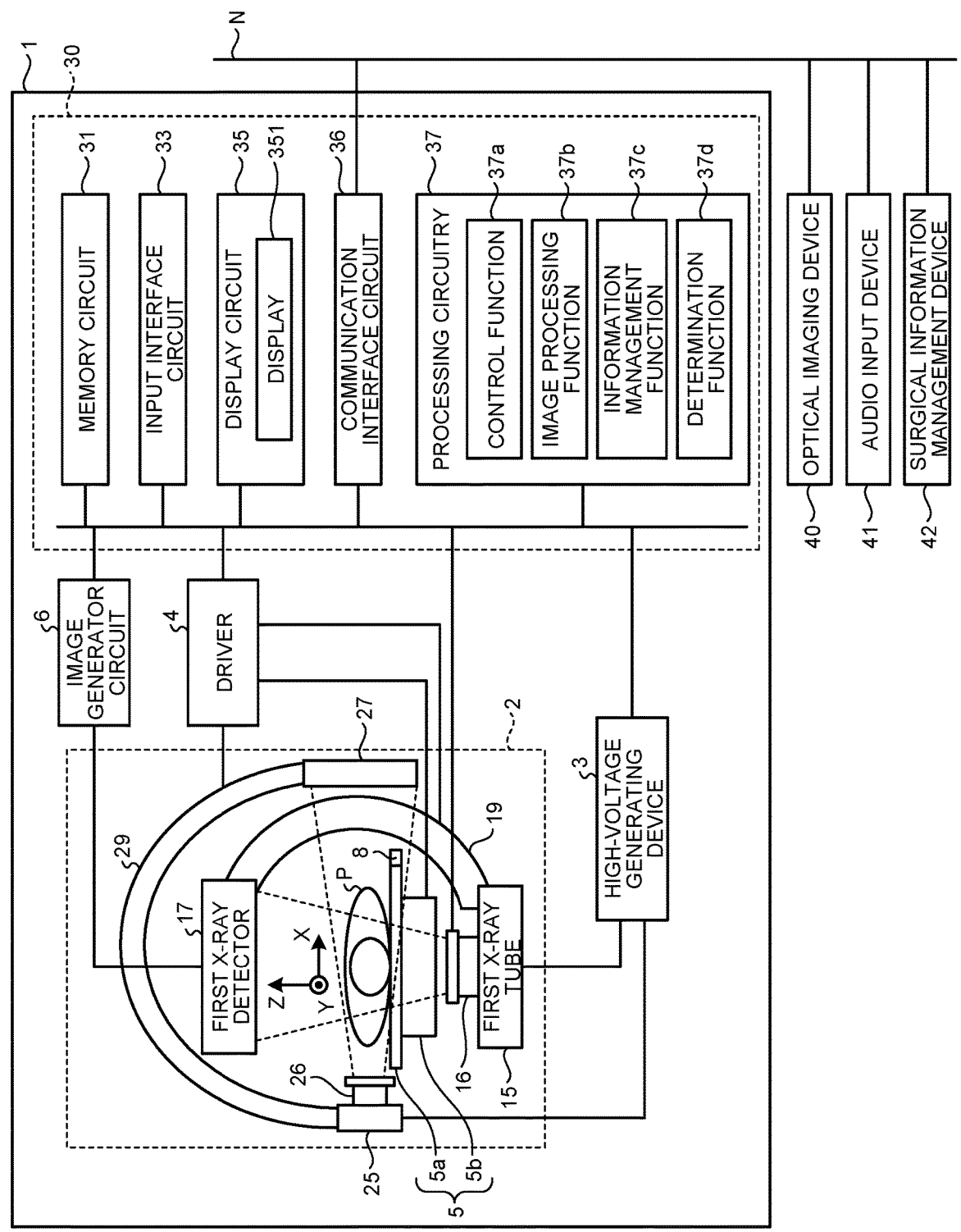
FIG. 1 illustrates an exemplary structure of an X-ray diagnosis system including an X-ray diagnosis apparatus according to an embodiment.

According to one embodiment, in general, a medical image diagnosis apparatus for use in a therapeutic procedure to a subject includes processing circuitry. The processing circuitry is configured to determine a status of a current therapeutic procedure; determine at least one proposed preset of settings of the medical image diagnosis apparatus according to the status of the current therapeutic procedure; and perform a control in accordance with the at least one proposed preset.

Hereinafter, a medical image diagnosis apparatus according to an embodiment will be described with reference to the accompanying drawings. The medical image diagnosis apparatus of an embodiment is used for monitoring a patient during a surgical procedure, for example. In the following, parts and elements denoted by the same reference numerals are considered to perform same or similar processing, therefore, an overlapping explanation thereof will be omitted when appropriate.

First Embodiment

The medical image diagnosis apparatus of a first embodiment is exemplified by an X-ray diagnosis apparatus for use in a surgical procedure.

FIG. 1 is a block diagram illustrating an exemplary structure of an X-ray diagnosis system S including an X-ray diagnosis apparatus 1 according to the first embodiment. As illustrated in FIG. 1, the X-ray diagnosis system S includes the X-ray diagnosis apparatus 1, an optical imaging device 40, an audio input device 41, and a surgical information management device 42. In the following, for the sake of specific explanation, the X-ray diagnosis apparatus 1 is exemplified by a biplane, cardiovascular X-ray diagnosis apparatus having two imaging systems.

The X-ray diagnosis apparatus 1 includes an imaging unit 2, a high-voltage generating device 3, a driver 4, a couch device 5, an image generator circuit, an operation unit 8, a memory circuit 31, an input interface circuit 33, a display circuit 35, a communication interface circuit 36, and processing circuitry 37. The memory circuit 31, the input interface circuit 33, the display circuit 35, the communication interface circuit 36, and the processing circuitry 37 are, for example, incorporated in the console device 30. The imaging unit 2 includes a first imaging system including a first X-ray tube 15, a first collimator 16, a first X-ray detector 17, and a first support mechanism 19; and a second imaging system including a second X-ray tube 25, a second collimator 26, a second X-ray detector 27, and a second support mechanism 29. The first support mechanism 19 and the second support mechanism 29 are also referred to as a C-arm mechanism and a Ω-arm mechanism due to their shapes, respectively. The moving direction of the first support mechanism 19 is along the C-form of the C-arm mechanism and referred to as C-direction. The moving direction of the second support mechanism 29 is along the Ω-form and referred to as Ω-direction.

The high-voltage generating device 3 includes electric circuits such as a transformer and a rectifier, a high-voltage generator, and an X-ray control device. The high-voltage generating device 3 functions to generate a high voltage to be applied to the first X-ray tube 15 and the second X-ray tube 25, and generate a filament current to be supplied to the first X-ray tube 15 and the second X-ray tube 25. The high-voltage generating device 3 controls an output voltage in accordance with X-rays irradiated by the first X-ray tube 15 and the second X-ray tube 25. The high-voltage generating device 3 can be either a transformer type or an inverter type.

The first X-ray tube 15 and the second X-ray tube 25 are vacuum tubes that generate, when applied with a high voltage and supplied with a filament current from the high-voltage generating device, respectively, an X-ray by emitting thermal electrons from the negative electrode (filament) to the positive electrode (target). The X-ray is generated by collision between the thermal electrons and the target. Examples of the first X-ray tube 15 and the second X-ray tube 25 include, but are not limited to, a rotating anode X-ray tube that generates an X-ray by irradiating the rotating anode with thermal electrons. The first X-ray tube 15 and the second X-ray tube 25 can be any type in addition to the rotating anode type.

The first collimator 16 and the second collimator 26 are disposed on the front surfaces of X-ray emission windows of the first X-ray tube 15 and the second X-ray tube 25, respectively. The first collimator 16 and the second collimator 26 each includes four diaphragm blades made of a metal plate such as lead. The diaphragm blades are driven by a driver (not illustrated) in accordance with a region of interest input by the operator through the input interface circuit 33, for example. The first collimator 16 and the second collimator 26 are driven by the driver to slide the diaphragm blades to thereby adjust an X-ray shielding area to any size. The first collimator 16 and the second collimator 26 work to shield the X-ray outside the aperture area by regulating the diaphragm blades. In this manner, the first collimator 16 and the second collimator 26 gather the X-rays emitted from the first X-ray tube 15 and the second X-ray tube 25 on a region of interest of a subject (patient) P.

The first X-ray detector 17 and the second X-ray detector 27 serve to detect the X-rays emitted from the first X-ray tube 15 and the second X-ray tube 25, respectively. The first X-ray detector 17 and the second X-ray detector 27 are, for example, flat panel detectors (hereinafter, referred to as FPD). Each FPD includes multiple semiconductor detection elements. There are two types of semiconductor detection elements, i.e., direct conversion and indirect conversion. Direct-conversion semiconductor detection elements directly convert X-rays into electric signals while indirect-conversion semiconductor detection elements use phosphor to convert X-rays into light and convert the light into electric signals. The FPD can be either type. The semiconductor detecting elements generate electric signals in response to an incident X-ray and output them to an analog to digital converter (not illustrated; hereinafter, referred to as A/D convertor). The A/D convertor converts the electric signals to digital data and outputs the digital data to the processing circuitry 37. Image intensifiers can be adopted for the first X-ray detector 17 and the second X-ray detector 27.

The driver 4 serves to drive the first support mechanism 19, the second support mechanism 29, and the couch device 5 under the control of the processing circuitry 37. For example, the driver 4 supplies a drive signal to the first support mechanism 19 in accordance with a control signal from the processing circuitry 37 to cause the first support mechanism 19 to slide in the C-direction and rotate in the direction orthogonal to the C-direction. The driver 4 supplies a drive signal to the second support mechanism 29 in accordance with a control signal from the processing circuitry 37 to cause the second support mechanism 29 to slide in the Ω-direction and rotate in the direction orthogonal to the Ω-direction. The driver 4 also supplies a drive signal to the couch device 5 in accordance with a control signal from the processing circuitry 37 to cause the couch device 5 to vertically and longitudinally move a table-top 5a.

The couch device 5 includes the table-top 5a on which a subject P to be scanned is laid and moved, and a base 5b that supports the table-top 5a.

The image generator circuit 6 serves to generate projection data in accordance with an output from the first X-ray detector 17 and the second X-ray detector 27.

The memory circuit (memory) is a storage device that stores various kinds of information, such as a hard disk drive (HDD), a solid state drive (SSD), or an integrated circuit memory, or a circuit including a combination of such storage devices. The memory circuit 31 stores therein, for example, projection data, image data, and programs corresponding to various functions to be read and performed by the processing circuitry 37. The memory circuit 31 can be a portable storage medium such as a compact disc (CD), a digital versatile disc (DVD), or a flash memory in addition to an HDD and a SDD, or can be a driver that reads and writes various kinds of information from and to a semiconductor memory device such as a random access memory (RAM). In addition, the memory circuit 31 may be located in an external storage device. The memory circuit 31 may include a plurality of storage devices and be partially connected via a network.

Further, the memory circuit 31 stores a preset-information management table. Herein, the term "preset" refers to settings of at least any of: a location of the imaging unit 2 of the X-ray diagnosis apparatus 1, an imaging method, a position of a display circuit 35 of the X-ray diagnosis apparatus 1, and a display layout of the display circuit 35. The term "preset information" refers to management information representing a preset of settings of the X-ray diagnosis apparatus 1, a surgical therapeutic procedure to be performed using the X-ray diagnosis apparatus 1, and a status of a therapeutic procedure in which the preset is used or selected, in association with one another. The expression, "status of a therapeutic procedure" (also simply referred to as a status) refers to information indicating in what stage a therapeutic procedure is during a surgical procedure concerned. A status of a therapeutic procedure may represent information at the time of occurrence of a certain event (that is, instantaneous information) or information in a certain period, such as "currently moving the catheter".

The preset information can be created from a preset history in previous surgical procedures performed using the X-ray diagnosis apparatus 1, a preset history in previous surgical procedures performed using another X-ray diagnosis apparatus 1, or else. The preset information can be created and managed for each physician or doctor or for each therapeutic procedure when appropriate. Further, the preset information can be automatically created during a surgical procedure, for example, from a preset used in the first half of a current therapeutic procedure, a status of the therapeutic procedure when the preset concerned is used, information as to the therapeutic procedure acquired from a surgical plan.

FIG. 2 illustrates an exemplary preset-information management table stored in the memory circuit 31. As illustrated in FIG. 2, the preset-information management table contains definitions of a plurality of sets of preset information with management numbers (No.) for management purpose. Each set of preset information includes a preset of settings of the X-ray diagnosis apparatus 1, a therapeutic procedure to be performed using the X-ray diagnosis apparatus 1, and a status of a therapeutic procedure in which the preset is used. For example, preset information 1 with management No. 1 is defined as information containing "cerebral aneurysm coil embolization" in the "therapeutic procedure" column, "start of catheter insertion" in the "status" column, and "angle is set to biplane reference position" and "adjust horizontal catheter insertion position to screen center" in the "preset" column. The preset-information management tables illustrated in FIG. 2 and FIG. 3 contain a "user ID" column to allow the management of preset information for each user (physician). In the user ID column, "default" signifies that the preset information is set to a recommended value or an initial value, and "A0001" signifies that the preset information is intended for a specific user with the ID No. concerned. The preset-information management table is not limited to the examples illustrated in FIG. 2 and FIG. 3, and can be the one excluding the user ID column to allow uniform management of the preset information according to recommended values.

FIG. 3 illustrates another exemplary preset-information management table stored in the memory circuit 31. In the preset-information management table illustrated in FIG. 3, preset information 100 with management No. 100 is defined as information containing "cerebral aneurysm coil embolization" in the "therapeutic procedure" column, "cerebral aneurysm analysis" in the "status" column, and "withdraw monitor to non-disturbing location to prepare for contrast injection" and "adjust horizontal catheter insertion position to screen center" in the "preset" column. These preset-information management tables are used in a later-described preset proposition process to select at least one proposed preset depending on the status of a therapeutic procedure.

The memory circuit 31 further stores a preset-history information management table. Herein, the term "preset-history information" refers to information representing an actually used preset in a current therapeutic procedure using the X-ray diagnosis apparatus 1, the current therapeutic procedure concerned, and a status of the therapeutic procedure when the preset is used, in association with one another for management purpose. Additionally, the preset-history information can include correction information. The correction information refers to information representing details of a correction of a selected preset of the X-ray diagnosis apparatus 1 made by the physician.

In the surgical procedure performed using the X-ray diagnosis apparatus 1, the preset-history information is created in real time with reference to, for example, the status of the current therapeutic procedure as determined by the processing circuitry 37. Thus, the preset-history information management table is updated upon every creation of new preset-history information. Additionally, the preset-history information can include supplementary information such as information on a current physician and temporal information (representing progress of a therapeutic procedure from a referential point in time, for example), when appropriate.

FIG. 4 illustrates an exemplary preset-history information management table stored in the memory circuit 31. As illustrated in FIG. 4, the preset-history information management table contains definitions of a plurality of sets of preset-history information with management numbers (No.) for management purpose. Each set of preset-history information includes a preset of settings of the X-ray diagnosis apparatus 1, a therapeutic procedure to be performed using the X-ray diagnosis apparatus 1, and a status of a therapeutic procedure in which the preset is used. For example, preset-history information 1 with management No. 1 is defined as information containing "cerebral aneurysm coil embolization" in the "therapeutic procedure" column, "start of catheter insertion" in the "status" column, "angle is set to biplane reference position" and "adjust horizontal catheter insertion position to screen center" in the "preset" column, and "adjust catheter insertion position to one-third of the screen in the bottom" in the "correction information" column. The preset-history information management table is used in a later-described preset proposition process to select at least one proposed preset depending on the status of a therapeutic procedure. The preset-history information management table in FIG. 4 corresponds to the preset-information management tables in FIG. 2 and FIG. 3 and includes the user ID column to allow the management of preset-history information for each user. However, when the preset-information management tables in FIG. 2 and FIG. 3 include no user ID column and the preset information is uniformly managed according to recommended values, the preset-history information management table includes no user ID column, either.

The memory circuit 31 further stores therein at least one proposed-preset determination rule. Herein, the proposed-preset determination rule refers to a definition of a criterion for determining whether to execute a proposed preset in the preset proposition process, such as "propose a preset having a use history of a number of times matching or exceeding a criterion (e.g., three times)". The proposed-preset determination rule can be created from a preset history in previous surgical procedures performed using the X-ray diagnosis apparatus 1 or a preset history in previous surgical procedures performed using another X-ray diagnosis apparatus 1, for example. Alternatively, an information management function 37c can dynamically create and update the proposed-preset determination rule by learning the preset-history information management table for the current therapeutic procedure. Further, the use of the proposed-preset determination rule may be such that a prepared proposed-preset determination rule is used in the first half of the surgical procedure, and then another proposed-preset determination rule is dynamically created and used by learning the preset-history information management table for the current therapeutic procedure, for example. Particular entities, e.g., physicians (doctors) or hospitals, may individually create and manage their own proposed-preset determination rules.

The memory circuit 31 also stores therein an image of the operating room transferred from the optical imaging device 40, audio data transferred from the audio input device 41, and surgical information transferred from the surgical information management device 42.

The input interface circuit 33 serves to receive various inputs from the operator and convert the inputs to electrical signals for output to the processing circuitry 37. For example, the input interface circuit 33 receives, from the operator, a manipulation to drive at least one of the imaging unit 2 and the couch device 5, an X-ray condition for X-ray generation, and/or an image processing condition for an image processing function 37b, for example. Examples of the input interface circuit 33 include, but are not limited to, a mouse, a keyboard, a trackball, a switch, a button, a joystick, a touch pad, and a touch panel, when appropriate. The input interface circuit 33 is, for example, mounted in the console device 30 installed in the control room different from the examination room.

In the first embodiment, the input interface circuit 33 is not limited to the one including physical operational components such as a mouse, a keyboard, a trackball, a switch, a button, a joystick, a footswitch, a touch pad, and a touch panel. Examples of the input interface circuit 33 further include an electric-signal processing circuit that receives an electric signal corresponding to an input from an external input device independent from the apparatus 1, to output the electric signal to the processing circuitry 37. Alternatively, the input interface circuit 33 may include a tablet terminal wirelessly communicable with the processing circuitry 37.

The display circuit 35 includes the display 351 that displays a medical image and else, an internal circuit that supplies a display signal to the display 351, and peripheral circuits such as a connector and/or a cable for connecting the display 351 and the internal circuit. The internal circuit serves to superimpose supplementary information, such as subject information and projection-data generation condition, on image data to generate display data. In turn the internal circuit performs D/A conversion and TV format conversion to the display data. The internal circuit allows the display 351 to display the display data after the conversions as a medical image. In addition the display circuit 35 displays a graphical user interface (GUI) for receiving various kinds of operations from the operator.

Examples of the display 351 include a liquid crystal display (LCD), a cathode ray tube (CRT) display, an organic electro luminescence display (OELD), a plasma display, and any display when appropriate. The display 351 may be a desk top display or may include a tablet terminal wirelessly communicable with the processing circuitry 37.

The communication interface circuit 36 is connected to an external device through a network. The communication interface circuit 36 serves to perform data communications with the external device through the network. Examples of the external device include, but are not limited to, a picture archiving and communication system (PACS) that manages various kinds of medical image data, and an electronic health record system that manages electronic health records with medical images attached. The communication standard between the communication interface circuit 36 and the external device can be any standard and may be exemplified by digital imaging and communications in medicine (DICOM).

The communication interface circuit 36 is also connected to external devices, i.e., the optical imaging device 40, the audio input device 41, and the surgical information management device 42 via a network N. The communication interface circuit 36 receives the image of the operating room from the optical imaging device 40, the audio data from the audio input device 41, and surgical-plan information containing patient information, physician information, and therapeutic-procedure information from the surgical information management device 42 via the network N. The image of the operating room, the audio data, and the surgical-plan information are successively stored, for example, in the memory circuit 31 upon receipt.

The processing circuitry 37 serves to control the operation of the X-ray diagnosis apparatus 1 as a whole in accordance with electric signals corresponding to inputs from the operation unit 8 or the input interface circuit 33. The processing circuitry 37 includes, for example, hardware resources including a processor such as a central processing unit (CPU), a micro processing unit (MPU), or a graphics processing unit (GPU), and a memory such as a read only memory (ROM) or a random access memory (RAM).

Various processing functions to be executed by the processing circuitry 37 are stored in the form of computer executable programs in the memory circuit 31. The processing circuitry 37 serves as a processor that reads and executes the programs to implement the functions corresponding to the programs. In other words, by reading the programs, the respective circuits acquire the functions corresponding to the programs.

Specifically, the processing circuitry 37 as a processor executes the programs loaded into the memory to implement a control function 37a, the image processing function 37b, the information management function 37c, and a determination function 37d. The processing circuitry 37 serving to implement the control function 37a, the image processing function 37b, the information management function 37c, and the determination function 37d corresponds to a controller, an information manager, and a determiner. The control function 37a, the image processing function 37b, the information management function 37c, and the determination function 37d may not be implemented by a single processing circuit. Processing circuitry can be configured of a combination of independent processors, so that the processors may individually implement the control function 37a, the image processing function 37b, the information management function 37c, and the determination function 37dc by executing the programs.

Alternatively, the processing circuitry 37 can be implemented by a processor such as an application specific integrated circuit (ASIC), a field programmable gate array (FPGA), another complex programmable logic device (CPLD), and a simple programmable logic device (SPLD).

The control function 37a of the processing circuitry 37 controls the driver 4, the high-voltage generating device 3, the first collimator 16, the second collimator 26, the memory circuit 31, the display circuit 35, the image processing function 37b, the information management function 37c, and the determination function 37d, in accordance with the operator's inputs through the operation unit 8 or the input interface circuit 33. Specifically, the control function 37a serves to read a control program from the memory circuit 31 and loads it into the memory in the processing circuitry 37 to control the respective elements of the X-ray diagnosis apparatus 1 according to the control program.

In a therapeutic procedure assist process as later described, the control function 37a performs control for at least one preset determined. For example, the control function 37a allows the display circuit 35 to display at least one preset (hereinafter, referred to as a proposed preset), which has been determined to be proposed in a preset proposition process. For another example, the control function 37a performs control of the settings of the X-ray diagnosis apparatus 1 with reference to a proposed preset selected by the physician from at least one proposed preset.

The image processing function 37b of the processing circuitry 37 serves to perform image processing, such as filtering, to the projection data from the image generator circuit 6 to generate image data. The image data corresponds to medical image data including a transparent image and a captured image of the subject P. The image processing function 37b performs, for example, synthesis and/or subtraction to the image data and outputs the resultant image data to the memory circuit 31 and the display circuit 35.

The information management function 37c of the processing circuitry 37 serves to generate and update the preset-history information management table. For example, the information management function 37c generates and updates the preset-history information management table by associating a preset selected during a current surgical procedure, a status of a therapeutic procedure as determined by the determination function 37d at the time of the preset selection, and an instruction as to a correction of the selected preset with one another, and writing them to the memory circuit 31 in real time.

The determination function 37d of the processing circuitry 37 serves to determine a status of a therapeutic procedure in real time on the basis of status information as to the therapeutic procedure concerned.

Herein, the status information as to a therapeutic procedure (hereinafter, simply referred to as status information) refers to information for use in determining the status of the therapeutic procedure concerned. Examples of the status information includes, but are not limited to, the medical image acquired by the X-ray diagnosis apparatus 1 during the therapeutic procedure, a three-dimensional image registration of the medical image acquired during the therapeutic procedure, the image of the operating room acquired by the optical imaging device 40, and the audio data acquired by the audio input device 41. The three-dimensional image registration of the medical image can be, for example, volume data acquired by another modality such as an X-ray CT apparatus, an MRI apparatus, an ultrasound diagnosis apparatus, or a nuclear medicine diagnosis apparatus, or a schematic three-dimensional image.

Specifically, the determination function 37d determines characteristic information of the status information such as the medical image, the image of the operating room, and the audio data acquired during the therapeutic procedure, to determine the status of the current therapeutic procedure on the basis of the characteristic information. Herein, the characteristic information refers to information indicating what objects are present, where and in what relationship they are located, and in what state they are.

For example, when the status information is the medical image acquired by the X-ray diagnosis apparatus 1 during the therapeutic procedure, examples of the characteristic information include locations (spatial coordinates), orientations (posture), sizes of objects (e.g., catheter, balloon, coil, stent, clip, anatomical landmark, treatment site, etc.) included in the medical image, and positional information on anatomical structures of the objects (e.g., the catheter is located inside the left atrium), and a positional relationship among the objects (e.g., the catheter is located three centimeters ahead of the mitral valve). Herein, the anatomical landmark refers to, for example, predefined anatomical locations such as the center of the left eyeball, the right pulmonic apex, and the aortic valve.

When the status information is the image of the operating room acquired by the optical imaging device 40 during the therapeutic procedure, for example, examples of the characteristic information include locations (spatial coordinates), orientations (postures), sizes (or physical builds), and behaviors or actions of objects (e.g., patient, physician, surgical instrument, contrast injector) included in the image of the operating room, and a positional relationship among the objects.

For another example, when the status information is the audio data acquired by the audio input device 41 during the therapeutic procedure, the characteristic information represents words acquired by speech recognition.

In addition, the characteristic information of the medical image and the image of the operating room can be obtained by, for example, object recognition, semantic segmentation, and/or behavior recognition. The characteristic information of the audio data can be obtained by speech recognition, for example.

Part of the determination function 37d may be located on the cloud. For example, the determination function 37d may determine the status of the therapeutic procedure by use of a speech recognition service provided through the Internet.

The determination function 37d of the processing circuitry 37 serves to determine the status of the therapeutic procedure in real time on the basis of the characteristic information of the status information as to the therapeutic procedure. The determination function 37d includes, for example, an artificial intelligence (AI) model such as a deep neural network that executes object recognition and semantic segmentation to inputs of the medical image, the image of the operating room, and the audio data to output the status of the therapeutic procedure. Alternatively, the determination function 37d may perform the determination using, for example, an AI model that receives the status information as to a therapeutic procedure and outputs the characteristic information, and a table containing the characteristic information and statuses of the therapeutic procedure in association with each other.

Further, the determination function 37d sends the status of the therapeutic procedure as determined to the information management function 37c. The information management function 37c receives the status of the therapeutic procedure from the determination function 37d and writes it to the preset-history information management table to update the preset-history information management table successively.

The determination function 37d also determines at least one proposed preset with reference to the preset-information management table, the preset-history information management table, and the proposed-preset determination rule. For example, the determination function 37d determines similarity between the status of the current therapeutic procedure and statuses of the therapeutic procedures contained in the preset-history information management table. The determination function 37d determines whether to propose a preset according to the determined similarity and the proposed-preset determination rule. The similarity between the status of the current therapeutic procedure and the statuses of the therapeutic procedures contained in the preset-history information management table can be determined, for example, by similarity between stages of state transition of the therapeutic procedures or similarity between status information based on which the status of the current therapeutic procedure has been determined and status information based on which the statuses of the therapeutic procedures contained in the preset-history information management table have been determined. In addition, to determine the similarity, it is possible to use an AI model that receives the status information based on which the status of the current therapeutic procedure has been determined as well as the status information based on which the statuses of the therapeutic procedures contained in the preset-history information management table have been determined, and outputs the similarity. In the present embodiment, the term "similarity" signifies a certain degree of similarity matching or exceeding a reference value.

After determining to propose a preset, the determination function 37d determines at least one proposed preset with reference to the preset-information management table and the preset-history information management table. The determination function 37d also corrects the proposed preset using correction information contained in the preset-history information management table.

Herein, the proposed preset determined by the determination function 37d can be not only a preset for implementing a particular setting with a fixed parameter but also a preset for implementing a dynamic setting which varies in value depending on each therapeutic procedure. Specifically, the preset for implementing a dynamic setting which varies in value depending on each therapeutic procedure can be exemplified by a preset for setting a working angle. The working angle refers to an easily maneuverable C-arm angle, which is set in the surgical planning for, for example, cerebral aneurysm coil embolization accompanied with radioscopy, or is set for analysis during such a surgical procedure. The working angle typically differs every time depending on the orientation of an aneurysm, for instance. Thus, in the case of using a preset that "working angle is applied when the status of the therapeutic procedure is coil placement", for example, the X-ray diagnosis apparatus 1 is set to use the working angle, however, the specific values of the working angle differ in every situation.

To determine whether to propose a preset, the determination function 37d may use another proposed-preset determination rule created by an AI model which is given inputs of present and previous preset-history information on the physician to output a proposed-preset determination rule, in addition to the proposed-preset determination rule stored in the memory circuit 31.

The optical imaging device 40 is, for example, a digital camera that captures an image of the room in which the X-ray diagnosis apparatus 1 is installed (for example, an operating room). The optical imaging device 40 successively captures and transfers images of the operating room to the X-ray diagnosis apparatus 1 via the network N.

The audio input device 41 serves to receive audio occurring in the operating room, e.g., the physician's voice, and successively transfers audio data to the X-ray diagnosis apparatus 1 via the network N.

The surgical information management device 42 serves to manage surgical-plan information. Herein, the surgical-plan information refers to information including a therapeutic procedure to be performed in a surgical procedure, a patient being a subject, a physician, date and time of the surgical procedure, instruments necessary for the surgical procedure, and so on. The surgical information management device 42 transmits the surgical-plan information to the X-ray diagnosis apparatus 1 via the network N.

Therapeutic Procedure Assist Process

The following will describe a therapeutic procedure assist process to be performed by the X-ray diagnosis apparatus 1 of the present embodiment. The therapeutic procedure assist process can be generally classified into a preset-history information generation process and a preset proposition process. In the following, the preset-history information generation process and the preset proposition process in the cerebral aneurysm coil embolization will be described by way of example, for the sake of specific explanation. This is, however, merely exemplary. Any therapeutic procedure can be a subject of the therapeutic procedure assist process as long as it uses the X-ray diagnosis apparatus 1 to observe images.

Preset-History Information Generation Process

FIG. 5 is a flowchart illustrating a preset-history information generation process. As illustrated in FIG. 5, the control function 37a receives a preset selection instruction (step S1), and the information management function 37c selects and records a preset in the preset-history information management table (step S2).

The information management function 37c then determines whether or not the control function 37a has received an instruction for correcting the settings of the preset (step S3). After determining that the control function 37a has received the instruction for correcting the settings of the preset (YES in step S3), the information management function 37c records details of the correction instruction received by the control function 37a in the preset-history information management table as correction information (step S4). After determining that the control function 37a has received no instruction for correcting the settings of the preset (NO in step S3), the information management function 37c proceeds to step S5.

The information management function 37c then acquires status information including at least one of the medical image acquired by the X-ray diagnosis apparatus 1, the image of the operating room acquired by the optical imaging device 40, and the audio data acquired by the audio input device 41 (step S5).

The determination function 37d determines the status of the current therapeutic procedure on the basis of the status information acquired by the information management function 37c (step S6).

For example, the determination function 37d recognizes a doctor's speech that "I am going to insert the catheter" through speech recognition of the acquired audio data and determines the status of the current therapeutic procedure as "start of catheter insertion", for example.

For another example, the determination function 37d can perform person/object recognition and behavior recognition to the acquired image of the operating room to recognize that a person is holding a catheter and in a posture to insert the catheter, for example. The determination function 37d determines the status of the current therapeutic procedure as, for example, "start of catheter insertion" from the result of the person/object recognition and behavior recognition.

For another example, the determination function 37d performs object recognition and semantic segmentation to the acquired medical image to determine locations, sizes, and a positional relationship of various objects, such as a catheter and an anatomical landmark, appearing in the medical image. The determination function 37d determines the status of the current therapeutic procedure as, for example, "catheter in motion" from a result of the object recognition and semantic segmentation.

For another example, the determination function 37d performs object recognition and semantic segmentation to the acquired medical image to determine whether the catheter has reached the head. After determining that the catheter has reached the head, the determination function 37d determines the status of the current therapeutic procedure as, for example, "catheter reaching the head".

For another example, the determination function 37d performs object recognition and semantic segmentation to the acquired medical image to determine whether the catheter has reached a contrast injection position. After determining that the catheter has reached the contrast injection position, the determination function 37d determines the status of the current therapeutic procedure as, for example, "cerebral aneurysm analysis".

In the cerebral aneurysm analysis, contrast-enhanced visualization is performed while contrast is being flowed into the brain from the entrance, to create a three-dimensional image of the cerebral aneurysm. The size, volume, and else of the aneurysm are calculated from the three-dimensional image to determine a placement method at the time of coil placement in the subsequent process. To the aneurysm having a large neck (root), for example, a placement method using a stent or a balloon to help the coil not protrude is adopted. To use the coil, a volume embolization ratio, i.e., a ratio between the volume of the aneurysm and the volume of the embolized coil is additionally calculated from the three dimensional image.

Subsequently, the information management function 37c records the status of the current therapeutic procedure as determined by the determination function 37d in the preset-history information management table (step S7).

Preset Proposition Process

Figure 6:
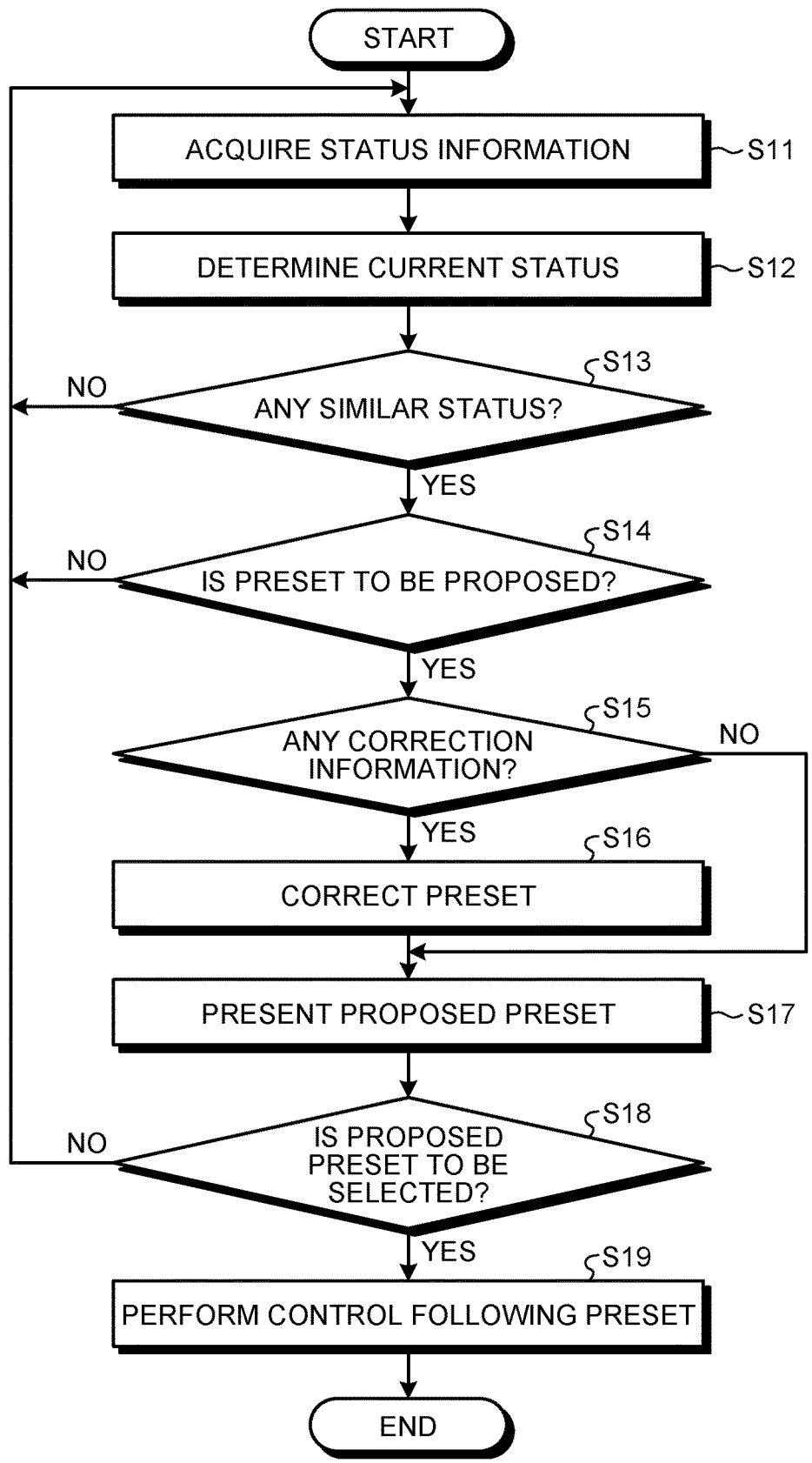
FIG. 6 a flowchart illustrating a preset proposition process to be executed by the X-ray diagnosis apparatus in an embodiment.

FIG. 6 is a flowchart illustrating a preset proposition process. As illustrated in FIG. 6, the information management function 37c acquires status information including at least one of the medical image acquired by the X-ray diagnosis apparatus 1, the image of the operating room acquired by the optical imaging device 40, and the audio data acquired by the audio input device 41 (step S11). The determination function 37d determines the status of the current therapeutic procedure on the basis of the status information acquired by the information management function 37c (step S12). Steps S11 and S12 are identical to steps S5 and S6.

The determination function 37d then refers to the preset-information management table to determine whether or not it contains a status similar to the status of the current therapeutic procedure as determined (step S13). After determining that the preset-information management table contains at least one status similar to the status of the current therapeutic procedure (YES in step S13), the determination function 37d proceeds to step S14. After determining that the preset-information management table contains no status similar to the status of the current therapeutic procedure (NO in step S13), the determination function 37d repeatedly performs the processing in steps S11 to S13.

The determination function 37d then determines whether to propose a preset with reference to the proposed-preset determination rule and the preset-history information management table (step S14). Assume that the proposed-preset determination rule be such that "a preset having a use history of three times or more is to be proposed", for example. In such a case, the determination function 37d determines, as a preset candidate, the preset having the status determined as being similar in step S13, to determine how many times the preset candidate has been used in the surgical procedure in question, with reference to the preset-history information management table. After determining that the preset candidate has been used three times or more in the surgical procedure in question (YES in step S14), the determination function 37d proceeds to step S15. After determining that the preset candidate has been used once or twice in the surgical procedure in question (NO in step S14), the determination function 37d repeatedly performs the processing in step S11 to S14.

Next, the determination function 37d refers to the preset-history information management table to determine whether or not it contains correction information representing a status similar to that in the preset candidate (step S15). After the determination function 37d determines that the preset-history information management table contains correction information representing a status similar to that in the preset candidate (YES in step S15), the information management function 37c corrects the preset candidate using the correction information (step S16).

As an example, assume that the preset candidate selected in step S13 be the preset with management No. 1 that "angle is set to biplane reference position" and "adjust horizontal catheter insertion position to screen center" in the preset-information management table of FIG. 2. In such a case the determination function 37d refers to, for example, preset-history information with management No. 1 indicating a status similar to the status "start of catheter insertion" of the preset candidate in the preset-history information management table of FIG. 3, to find correction information representing "adjust catheter insertion position to one-third of the screen in the bottom". The information management function 37c corrects part of the preset candidate that "adjust horizontal catheter insertion position to screen center" to "adjust catheter insertion position to one-third of the screen in the bottom" according to the correction information. By such a correction, the proposed preset can reflect a physician's inclination to see more current information first on the medical image.

As another example, assume that the preset candidate selected in step S13 be the preset with management No. 4 representing "biplane reference position" in the preset-information management table of FIG. 2. In such a case the determination function 37d refers to, for example, preset-history information with management No. 2 indicating a status similar to the status "catheter in motion" of the preset candidate in the preset-history information management table of FIG. 4, to find correction information representing "move FPD toward the patient as close as possible but not to contact the patient". The information management function 37c corrects part of the preset candidate "biplane reference position" to "move FPD toward the patient as close as possible but not to contact the patient" according to the correction information. By such a correction the proposed preset can include adjustment of radioscopy during the therapeutic procedure so as to reduce scattered rays.

As another example, assume that the preset candidate selected in step S13 be the preset with management No. 3 representing "biplane reference position" and "move FPD toward the patient as close as possible but not to contact the patient" in the preset-information management table of FIG. 2. In such a case the determination function 37d refers to, for example, preset-history information with management No. 2 indicating a status similar to the status "catheter in motion" of the preset candidate in the preset-history information management table of FIG. 4, to find correction information representing "move FPD to the patient as close as possible but not to contact the patient". The preset candidate already reflects the correction information, so that the preset candidate is not to be corrected.

As another example, assume that the preset candidate selected in step 313 be the preset with management No. 9 that "tilt of C-arm is preset or set to automatically set working angle" or "adjusted to center of the right or left brain having aneurysm" in the preset-information management table of FIG. 2. In such a case the determination function 37d refers to, for example, preset-history information with management No. 6 indicating a status similar to the status "coil placement" of the preset candidate in the preset-history information management table of FIG. 4, to find correction information representing "adjust horizontal and vertical motion around aneurysm". The information management function 37c corrects part of the preset candidate "adjusted to center of the right or left brain having aneurysm" to "adjust horizontal and vertical motion around aneurysm" according to the correction information.

As another example, assume that the preset candidate selected in step S13 be the preset with management No. 100 that "withdraw monitor to non-disturbing location to prepare for contrast injection" in the preset-information management table of FIG. 3. In such a case the determination function 37d refers to, for example, preset-history information indicating a status similar to the status "coil placement" of the preset candidate in the preset-history information management table, to determine whether it contains correction information. After finding correction information, the information management function 37c corrects the preset candidate according to the correction information. If finding no correction information, the information management function 37c does not correct the preset candidate.

As another example, assume that the preset candidate selected in step S13 be the preset with management No. 103 that "change monitor to MPR image (three orthogonal-plane image) display layout" in the preset-information management table of FIG. 3. In such a case the determination function 37d refers to, for example, preset-history information indicating a status similar to the status "generate three-dimensional image for cerebral aneurysm analysis" of the preset candidate in the preset-history information management table, to determine whether it contains correction information. After finding correction information, the information management function 37c corrects the preset candidate according to the correction information. If finding no correction information, the information management function 37c does not correct the preset candidate.

Meanwhile, when the determination function 37d determines that there is no correction information associated with the preset candidate (NO in step S15), the flow proceeds to step S17.

Next, the control function 37a allows the display 351 to present or display, as a proposed preset, the preset candidate corrected with the correction information found in step S16 or the preset candidate determined in step S14 in the case of no correction information found (step S14). When appropriate, the control function 37a outputs audio data representing the details of the proposed preset from the speaker. The control function 37a allows the display 351 to present an inquiry as to execution or non-execution of the proposed preset together with the proposed preset. If two or more preset candidates are found, the preset candidates can be individually subjected to the processing in steps S14 to S17, to be displayed on the display 351.

Next, the control function 37a determines whether the proposed preset has been selected (i.e., whether to have received an instruction for executing a proposed preset (step S18). In response to receipt of an instruction for executing a proposed preset through the input interface circuit 33 (YES in step S18), the control function 37a performs a control in accordance with the proposed preset (step S19). In the case of the proposed preset including "adjust catheter insertion position to one-third of the screen in the bottom", for example, the control function 37a controls the display circuit 35 to display the catheter insertion position at one-third of the screen in the bottom on the display 351. For another example, in the case of the proposed preset including "change monitor to MPR image (three orthogonal-plane image) display layout", the control function 37a controls the image processing function 37b and the display circuit 35 to display the MPR image (three orthogonal-plane image).

Without receipt of the instruction for executing the proposed preset through the input interface circuit 33 (No in step S18), the processing in steps S11 to S18 is repeated.

FIGS. 7A to 7E illustrate an exemplary presentation form of the proposed preset in step S17. In the example of FIG. 7A to 7E, assume that the proposed preset be the preset with management No. 5 including the status that "catheter in motion (reaching screen top end)" and "move C-arm in parallel following moving catheter" in the preset-information management table of FIG. 2. In the present embodiment the first support mechanism 19 (C-arm) or the second support mechanism 29 (Ω-arm) is considered to automatically move in parallel in the horizontal direction, for the sake of specific explanation. Alternatively, the angle of the first support mechanism 19 or the second support mechanism 29 can be automatically set by automatic positioning, and the movement of the visual field with respect to the patient's body axis can be adjusted by sliding the table-top 5a of the couch device 5.

Figure 7A:
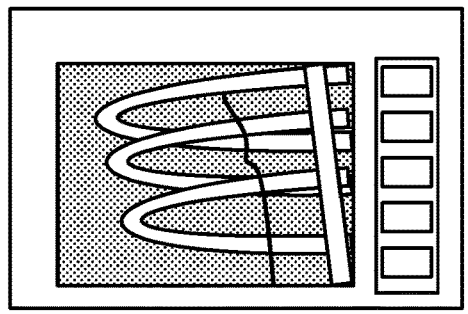
FIGS. 7A to 7E illustrate an example of presentation form of a proposed preset by the X-ray diagnosis apparatus in an embodiment.

As illustrated in FIG. 7A, the catheter has reached the top end of the screen on the medical image displayed on the display 351. Triggered by the catheter's arrival at the top end of the screen, the determination function 37d performs the processing in steps S11 to S16 of FIG. 6 to determine the proposed preset "move C-arm in parallel following moving catheter".

Figure 7B:
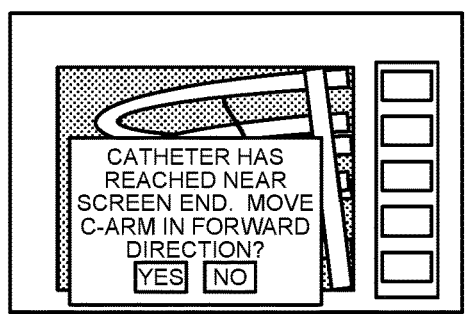
Figure 7C:
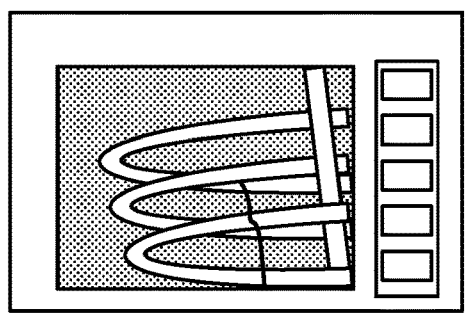
Figure 7D:
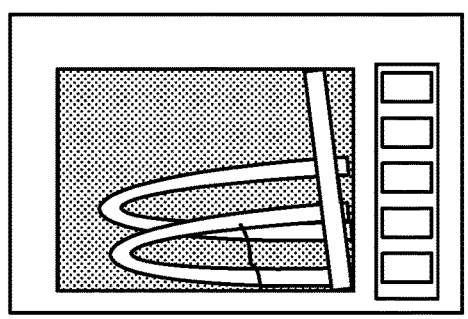
Figure 7E:
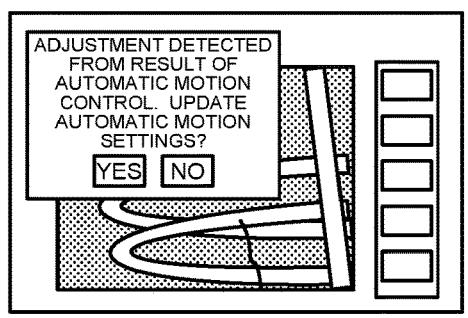

As illustrated in FIG. 7B, for example, the control function 37a displays the proposed preset and an inquiry as to execution or non-execution of the proposed preset on the display 351. In response to receipt of an instruction for execution of the proposed preset (selection of "Yes" in FIG. 7B) through the input interface circuit 33, the control function 37a controls the first support mechanism 19 (C-arm) to move in parallel following the moving catheter in accordance with the proposed preset selected in step S18. As a result, the display 351 displays the medical image depicting that the first support mechanism 19 (C-arm) is following the moving catheter, as illustrated in FIGS. 7C and 7D. In response to receipt of an instruction for non-execution of the proposed preset through the input interface circuit 33 (selection of "No" in FIG. 7B), the control function 37 refrains from updating the automatic-motion settings.

In the case of detecting, for example, an adjustment of the working angle from a result of automatic motion control after the control (setting) in accordance with the proposed preset, the control function 37a displays an inquiry as to whether to update the automatic-motion settings on the display 351. In response to receipt of an instruction for updating the automatic-motion settings through the input interface circuit 33 (selection of "Yes" in FIG. 7E), the control function 37 updates the automatic-motion settings. In response to receipt of an instruction for not updating the automatic-motion settings through the input interface circuit 33 (selection of "No" in FIG. 7E), the control function 37 refrains from updating the automatic-motion settings.

As described above, the X-ray diagnosis apparatus 1 as the medical image diagnosis apparatus according to the present embodiment includes the determination function 37d serving as a determiner and the control function 37a serving as a controller. The determination function 37d determines the status of the current therapeutic procedure, to determine at least one proposed preset of the settings of the medical image diagnosis apparatus according to the status of the current therapeutic procedure as determined. The control function 37a performs control related to the at least one preset as determined.

Thus, the X-ray diagnosis apparatus 1 can determine at least one preset that the physician currently requires or will require later in the therapeutic procedure concerned according to the status of the current therapeutic procedure, to present the preset to the physician as a proposed preset. This makes it possible for the physician to correctly and quickly select a preset suitable for the current situation of the therapeutic procedure without selecting a desired preset from multiple presets represented by buttons or thumbnail images, for example.

In the surgical procedure or IVR, time matters so that higher efficiency is requested. In view of a shortage of medical resources due to aging of population or the reform of working practices, higher efficiency has been on increased demand in recent years. The X-ray diagnosis apparatus 1 according to the present embodiment can alleviate a burden on the physician in using the preset function of the X-ray diagnosis apparatus, and help the physician focus on his or her own manipulation. This results in implementing improved efficiency in the situation as a surgical procedure or IVR.

Second Embodiment

The following will describe an ultrasound diagnosis apparatus for use in a surgical procedure as an example of a medical image diagnosis apparatus according to a second embodiment.

Figure 8:
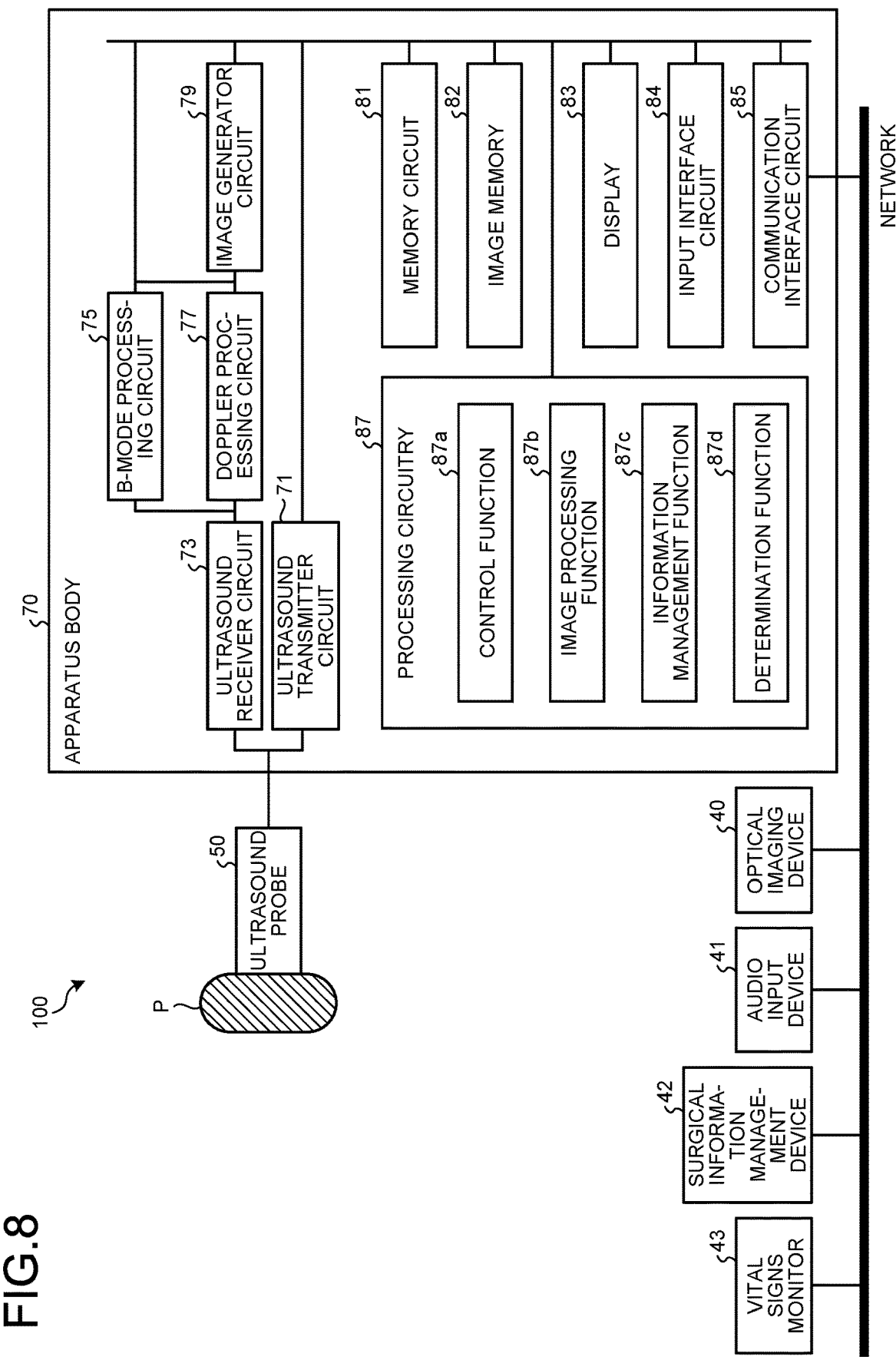
FIG. 8 is a block diagram illustrating an exemplary structure of an ultrasound diagnosis apparatus according to an embodiment.

FIG. 8 is a block diagram illustrating an exemplary structure of an ultrasound diagnosis system including an ultrasound diagnosis apparatus 100 of the second embodiment. As illustrated in FIG. 8, the ultrasound diagnosis system includes the ultrasound diagnosis apparatus 100, an optical imaging device 40, an audio input device 41, a surgical information management device 42, and a vital signs monitor 43.

The vital signs monitor 43 serves to measure vital information (i.e., heart rate, respiration rate, blood pressure, and body temperature) of the subject P. The vital signs monitor 43 transfers the vital information as measured to the ultrasound diagnosis apparatus 100 via the network N. The vital signs monitor 43 includes an alert function to monitor numerical values (for example, blood pressure) included in the vital information and alert the physician when the numerical values satisfy an alert condition (for example, falling to a reference value or below).

The ultrasound diagnosis apparatus 100 includes an ultrasound probe 50 and an apparatus body 70.

The ultrasound probe 50 includes, for example, a plurality of piezoelectric vibrators, matching layers included in the piezoelectric vibrators, and a backing material that prevents ultrasonic waves from propagating backward from the piezoelectric vibrators. The ultrasound probe 50 is detachably connected to the apparatus body 70. The piezoelectric vibrators are supplied with a drive signal from an ultrasound transmitter circuit 71 in the apparatus body 70 and generates ultrasonic waves in accordance with the drive signal. The ultrasound probe 50 may be provided with a button which is pressed for various kinds of operation such as freeze operation.

The ultrasound probe 50 transmits ultrasonic waves to the subject P. The transmitted ultrasonic waves are consecutively reflected at the discontinuous planes of acoustic impedance through the body tissues of the subject P. The reflected ultrasonic waves, i.e., a reflected wave signal (hereinafter, referred to as echo signal), are received by the piezoelectric vibrators of the ultrasound probe 50. The amplitude of the received echo signal depends on a difference in acoustic impedance at the discontinuous planes reflecting the ultrasonic waves. When the transmitted ultrasonic waves are reflected by the bloodstream or the cardiac wall surface, the echo signal typically undergoes a frequency shift due to the Doppler effect depending on a velocity component of a moving object with respect to the transmission direction of the ultrasonic waves. The ultrasound probe 50 receives and converts the echo signal from the subject P into an electric signal. In the present embodiment, the ultrasound probe 50 is defined as an oral probe.

The apparatus body 70 serves to generate an ultrasound image in accordance with the echo signal received by the ultrasound probe 50. As illustrated in FIG. 8, the apparatus body 70 includes an ultrasound transmitter circuit 71, an ultrasound receiver circuit 73, a B-mode processing circuit 75, a doppler processing circuit 77, an image generator circuit, a memory circuit (storage) 81, an image memory 82 (also referred to as cine memory or cache), a display 83, the input interface circuit 84, a communication interface circuit 85, and processing circuitry 87.

The ultrasound transmitter circuit 71 serves as a processor that supplies the drive signal to the ultrasound probe 50. The ultrasound transmitter circuit 71 includes, for example, a trigger generator circuit, a delay circuit, and a pulsar circuit. The trigger generator circuit serves to repeatedly generate rate pulses for forming transmission ultrasonic waves at a given frequency under the control of a control function 87a of the processing circuitry 87. The delay circuit serves to apply a delay time to each pulse. The delay time is set to each of the piezoelectric vibrators and refers to a time taken for converging the ultrasonic waves from the ultrasound probe 50 in a beam form to set a transmission directivity thereof. The pulsar circuit serves to apply a drive signal (drive pulse) to the ultrasound probe 50 at timing based on each pulse under the control of the control function 87a. The delay circuit applies different amounts of delay time to the individual pulses, thereby making it possible to adjust the transmission direction from each piezoelectric vibrator surface in a desired manner.

The ultrasound receiver circuit 73 serves as a processor that performs various kinds of processing to the echo signal received by the ultrasound probe 50 to generate a reception signal. The ultrasound receiver circuit 73 includes, for example, an amplifier circuit, an A/D converter, a reception delay circuit, and an adder. The amplifier circuit serves to amplify the echo signal received by the ultrasound probe 50 for each channel and subject the amplified echo signal to gain correction. The A/D converter serves to convert the gain-corrected echo signal to a digital signal. The reception delay circuit serves to apply, to the digital signal, a delay time taken for setting a reception directivity. The adder serves to add multiple digital signals given respective delay times. Through the adding process of the adder, the ultrasound receiver circuit 73 can generate a reception signal having an enhanced reflective component from the direction corresponding to the reception directivity.

The B-mode processing circuit 75 serves to receive the reception signal from the ultrasound receiver circuit 73 to generate B-mode data in accordance with the reception signal. The B-mode processing circuit 75 performs, for example, envelop demodulation and logarithmic amplification to the reception signal from the ultrasound receiver circuit 73, to generate data representing signal intensity by a degree of brightness (i.e., data obtained in B-mode, hereinafter referred to as B-mode data). The generated B-mode data is B-mode raw data on the two-dimensional ultrasound scanning line and is stored in a raw data memory (not illustrated).

The doppler processing circuit 77 serves as a processor that receives the reception signal from the ultrasound receiver circuit 73 to generate dopplar waveform data and dopplar data in accordance with the reception signal. The doppler processing circuit 77 serves to extract a bloodstream signal from the reception signal to generate dopplar waveform data from the bloodstream signal and generate data representing information, extracted from the bloodstream signal, such as average velocity, distribution, and power at a large number of points (i.e., data obtained in dopplar mode, hereinafter referred to as dopplar data). The generated dopplar data is dopplar raw data on the two-dimensional ultrasound scanning line and is stored in a raw data memory (not illustrated).

The image generator circuit 79 serves to generate a GUI (graphic user interface) that allows the operator to input various instructions through the input interface circuit 84. The image generator circuit 79 serves as a processor having a function (scan converter) of generating various kinds of ultrasound image data based on the data generated by the B-mode processing circuit 75 and the doppler processing circuit 77. The image generator circuit 79 includes an internal memory (not illustrated). The image generator circuit 79 generates two-dimensional ultrasound image data composed of pixels (such as B-mode image data, dopplar color image data, dopplar waveform image data) by raw to pixel conversion. The image generator circuit 79 stores the ultrasound image data in the memory circuit 81. The image generator circuit 79 performs various kinds of processing including dynamic range, brightness, contrast, and y-curve corrections and RGB conversion to the ultrasound image data.

Additionally, the image generator circuit 79 can generate volume data composed of voxels in a desired range by performing interpolation to the B-mode image data to add spatial position information, for example. The image generator circuit 79 may generate volume data by performing raw to voxel conversion including the interpolation for adding spatial position information, to the B-mode raw data stored in the raw data memory. Further, the image generator circuit 79 may generate, for example, a rendering image or a multi-planar reconstruction (MPR) image by performing rendering or multi-planar reconstruction to various kinds of volume data.

The memory circuit 81 is implemented by, for example, a magnetic or optical storage medium or a processor-readable storage medium such as an integrated circuit memory. For example, the memory circuit 81 corresponds to an HDD, an SSD, or a semiconductor memory that stores various kinds of information. In addition to an HDD or an SSD, the memory circuit 81 may be a portable storage medium such as a CD, a DVD, or a flash memory, or a driver that reads and writes various kinds of information from and to a semiconductor memory device as a RAM.

The memory circuit 81 stores programs to implement various functions according to the present embodiment. The memory circuit 81 stores a data group such as diagnostic information (for example, patient ID, doctor's observation, etc.), diagnostic protocol, a body mark generation program, and a conversion table for use in presetting the range of color data for visualization in unit of a site to be diagnosed. The control function 87a can transfer the various kinds of data from the memory circuit 81 to an external device through the communication interface circuit 85.

Further, the memory circuit 81 stores therein a preset-information management table, a preset-history information management table, and at least one proposed-preset determination rule.

FIG. 9 illustrates an exemplary preset-information management table stored in the memory circuit 81. As illustrated in FIG. 9, for example, preset information 1 with management No. 1 is defined as information containing "mitral valve clipping" in the "therapeutic procedure" column, "clip approaching the valve" in the "status" column, and "midesophagus commissural image (two chamber view: 60 to 90 degrees)" and "midesophagus aortic valve long axis image (three chamber view: 100 to 160 degrees)" in the "preset" column. Herein, the mitral valve clipping refers to a procedure that attaches, using the catheter, a clip to a failed portion of the mitral valve in the heart causing regurgitation in order to treat the regurgitation. The preset-information management table of FIG. 9 contains the "user ID" column to manage the preset information for each user or physician by way of example, as with FIG. 2 and FIG. 3. The preset-information management table can exclude the "user ID" column to allow uniform management of the preset information according to recommended values.

For another example, preset information 100 with management No. 100 is defined as information containing "mitral valve clipping" in the "therapeutic procedure" column, "clip attachment" in the "status" column, and "propose for changing alert condition to set clip attachment mode" in the "preset" column.

The preset, "propose for changing alert condition to set clip attachment mode" is further described. In the mitral valve clipping, the clip is attached to a regurgitated portion of the mitral valve to treat the regurgitation. By the clip attachment, the mitral valve becomes partially non-openable, resulting in temporarily lowering the blood pressure. This temporary drop in the blood pressure occurs due to proper attachment of the clip to the mitral valve, therefore, it is considered as normal. However, the signs monitor 43 issues an alert if the temporary drop in the blood pressure satisfies the alert condition. Thus, the preset, "propose for changing alert condition to set clip attachment mode" is intended for preventing the vital signs monitor 43 being an external device from issuing an alert in response to a temporal drop in the blood pressure caused by the clip attachment, by changing the alert condition when the "status" indicates "clip attachment".

The preset-history information management table and at least one proposed-preset determination rule are basically the same as in the first embodiment, therefore, a description thereof is omitted.

The memory circuit 81 further stores therein the image of the operating room transferred from the optical imaging device 40, the audio data transferred from audio input device 41, the surgical information transferred from the surgical information management device 42, and the vital information transferred from the vital signs monitor 43.

The image memory 82 includes, for example, a processor-readable storage medium such as a semiconductor memory. The image memory 82 is implemented by, for example, a cache memory. The image memory 82 stores therein, for example, various kinds of image data obtained in a certain period before an input of the freeze operation through the input interface circuit 84. Specifically, the image memory 82 stores therein dopplar waveform image data obtained in a certain previous period from the instance at which the freeze button is pressed for a scroll display, in such a manner as to prevent the dopplar waveform image data from being overwritten with another data. The memory circuit 81 and the image memory 82 may be united together as a single storage device.

The display 83 can be, for example, any display such as a liquid crystal display, a CRT display, an organic EL display, or a plasma display. The display 83 may be embedded in the apparatus body 70. In addition, the display 83 may be a desk top display or include a tablet terminal wirelessly communicable with the apparatus body 70. The display 83 is an exemplary display circuit.

The display 83 serves to display various kinds of information. The display 83 displays, for example, the ultrasound image generated by the processing circuitry 87 and a graphic user interface (GUI) for receiving various operations from the operator. In cineradiography display mode, the display 83 displays ultrasound images in time series in response to an operator's instruction through the input interface circuit 84. In scroll display mode the display 83 displays dopplar waveform images in time series in response to an operator's instruction through the input interface circuit 84. In dopplar mode, for example, in response to an input of a scroll operation after the freeze operation (scroll display), the display 83 displays a dopplar waveform corresponding to at least one heartbeat in accordance with the direction and amount of the scroll operation.

The input interface circuit 84 serves to receive various kinds of inputs from the operator to convert the inputs to electric signals and output them to the processing circuitry 87. The input interface circuit 84 includes, for example, a mouse, a keyboard, a trackball, a switch, a button, a joystick, a touch pad, and a touch panel display. In the present embodiment the input interface circuit 84 is not limited to the one including physical operational components such as a mouse, a keyboard, a trackball, a switch, a button, a joystick, a touch pad, and a touch panel display. Examples of the input interface circuit 84 include electric-signal processing circuitry that receives an electric signal corresponding to an input from an external input device independent from the input interface circuit 84, and outputs the electric signal to the processing circuitry 87. The input interface circuit 84 may not be included in the apparatus body 70. The input interface circuit 84 may include a tablet terminal wirelessly communicable with the apparatus body 70, for example.

In response to a press onto an end button or a freeze button (hereinafter, referred to as freeze operation) provided in the input interface circuit 84, for example, the ultrasound diagnosis apparatus 100 stops transmitting and receiving ultrasonic waves and is placed in a temporary stop state.

In response to a freeze operation through the input interface circuit 84 during scanning in the B-mode, the ultrasound diagnosis apparatus 100 transitions from a real-time display mode in which an ultrasound image generated based on transmitted and received ultrasonic waves is displayed in real time to the cineradiography display mode in which multiple ultrasound images stored in the image memory 82 can be displayed in time series (hereinafter, referred to as cineradiography display).

Further, in response to a freeze operation through the input interface circuit 84 during scanning in the dopplar mode, the ultrasound diagnosis apparatus 100 transitions from a real-time display mode in which dopplar waveforms generated based on transmitted and received ultrasonic waves are displayed in real time to a scroll display mode. Herein, the scroll display mode refers to a display mode in which multiple dopplar waveform images stored in the image memory 82 can be scrolled forward or backward in time series on the display. In the scroll display mode, for example, along with rotation of the trackball manipulated by the physician, the ultrasound diagnosis apparatus 100 reads and displays a dopplar waveform image corresponding to the direction and amount of the rotation of the trackball from among the dopplar waveform images stored in the image memory 82. The rotation of the trackball corresponds to a scroll operation to scroll chronological dopplar waveform images forward or backward in time series after the input of the freeze operation.

The communication interface circuit 85 includes substantially the same functions as the communication interface circuit 36, therefore, a description thereof is omitted.

The processing circuitry 87 is, for example, a processor functioning as the center of the ultrasound diagnosis apparatus 100. The processing circuitry 87 includes hardware resources such as a processor as a CPU or a MPU and a memory as a ROM or RAM. The processing circuitry 87 may be implemented by an application specific integrated circuit, a field programmable gate array, another complex programmable logic device, or a simple programmable logic device.

The processing circuitry 87 includes, for example, various kinds of functions such as the control function 87a, an image processing function 87b, an information management function 87c, and a determination function 87d. The processing circuitry 87 loads various kinds of programs from the memory circuit 81 into its own memory and executes them to implement the control function 87a, the image processing function 87b, the information management function 87c, and the determination function 87d. Alternatively, the programs can be directly incorporated in the circuit of the processor, in place of being stored in the memory circuit 81. In this case the processor reads and executes the programs from the circuit to implement the respective functions.

The processing circuitry 87 serving to implement the control function 87a, the information management function 87c, and the determination function 87d corresponds to a controller, an information manager, and a determiner. The control function 87a, the image processing function 87b, the information management function 87c, and the determination function 87d may not be implemented by a single processing circuit. Multiple independent processors can be combined to form processing circuitry, so that the individual processors can implement the control function 87a, the image processing function 87b, the information management function 87c, and the determination function 87d by executing the programs.

The functions related to the therapeutic procedure assist process to be implemented by the control function 87a, the image processing function 87b, the information management function 87c, and the determination function 87d are substantially the same as the control function 37a, the image processing function 37b, the information management function 37c, and the determination function 37d in the first embodiment, therefore, a description thereof is omitted.

Therapeutic Procedure Assist Process

The following will describe a therapeutic procedure assist process to be executed by the ultrasound diagnosis apparatus 100 of the present embodiment, by way of example. For the sake of specific explanation, the present embodiment describes use of a transesophageal ultrasound diagnosis apparatus as an example of the ultrasound diagnosis apparatus 100 when performing a therapeutic procedure, for example, placing a clip such as a MitraClip (registered trademark) in the mitral valve (mitral valve clipping).

The mitral valve clipping is, for example, generally performed in three steps, as follows. That is, in the first step the catheter is moved to the mitral valve of the heart while being observed using the X-ray diagnosis apparatus 1. In the second step a clip delivery system including a clip at the tip end is inserted into the catheter to place the clip while being observed with the ultrasound diagnosis apparatus 100. For example, the physician moves the clip closer to the mitral valve while monitoring a two-dimensional image (such as a two chamber view, a three chamber view) using the ultrasound diagnosis apparatus 100, and adjusts the angle of the clip while monitoring a three-dimensional image using the ultrasound diagnosis apparatus 100. After the angle adjustment, the physician then inserts the clip into the left ventricle from the left atrium to attach the clip. In the third step the mitral valve is subjected to fluoroscopy again by the X-ray diagnosis apparatus 1 and the ultrasound diagnosis apparatus 100 for the purpose of observation after the placement. The following will describe an example of applying the therapeutic procedure assist process in the second step.

Preset-History Information Generation Process

Referring to FIG. 5, the preset-history information generation process to be performed by the ultrasound diagnosis apparatus 100 is described.

As illustrated in FIG. 5, the control function 87a receives a preset selection instruction (step S1), and the information management function 87c selects and records a preset in the preset-history information management table (step S2).

The information management function 87c then determines whether or not the control function 87a has received an instruction for correcting the settings in the preset (step S3). After determining that the control function 87a has received the instruction for correcting the settings in the preset (YES in step S3), the information management function 87c records, in the preset-history information management table, correction information representing the details of the correction instruction received by the control function 87a (step S4). After determining that the control function 87a has received no instruction for correcting the settings in the preset (NO in step S3), the information management function 87c proceeds to step S5.

The information management function 87c then acquires status information including at least one of the medical image acquired by the ultrasound diagnosis apparatus 100, the image of the operating room acquired by the optical imaging device 40, and the audio data acquired by the audio input device 41 (step S5).

The determination function 87d then determines a status of the current therapeutic procedure based on the status information acquired by the information management function 87c (step S6).

For example, the determination function 87d recognizes a doctor's statement that "I am going to insert the clip delivery system into the catheter to start clip placement" through speech recognition of the acquired audio data, and determines the status of the current therapeutic procedure as, for example, "clip approaching the valve".

For another example, the determination function 87d performs person/object recognition and behavior recognition to the image of the operating room to recognize that a person is holding a clip delivery system and in a posture to insert the clip delivery system into the catheter. The determination function 87d determines the status of the current therapeutic procedure as, for example, "clip approaching the valve" from the result of the person/object recognition and behavior recognition.

For another example, the determination function 87d performs object recognition and semantic segmentation to the medical image as acquired, to determine that the catheter is already inserted into the left atrium. The determination function 87d determines the status of the current therapeutic procedure as, for example, "clip approaching the valve" from the fact that the catheter is already inserted into the left atrium.

For another example, the determination function 87d performs object recognition and semantic segmentation to the medical image as acquired, to determine a positional relationship between the clip and the mitral valve. The determination function 87d also detects a motion vector of the catheter in the moving direction toward the mitral valve. When the distance between the clip and the mitral valve decreases to a certain value or less (e.g., the absolute value of an average motion during a certain period is a threshold or less) and the motion vector is a certain value or less, the determination function 87d determines a transition of the status of the current therapeutic procedure from "clip approaching the valve" to "clip angle adjustment", for example. Herein, the determination criterion is defined as "when the distance between the clip and the mitral valve decreases to a certain value or less and the motion vector is a certain value or less" since the distance between the clip and the mitral valve will never take a constant value (e.g., zero) because of a body motion or else.

Subsequently, the information management function 37c records the status of the current therapeutic procedure as determined by the determination function 37d in the preset-history information management table (step S7).

Through the processing in steps S1 to S7 as described above, the preset-history information is generated in response to the selection of the preset.

Preset Proposition Process

With reference to FIG. 6, a preset proposition process to be executed by the ultrasound diagnosis apparatus 100 will be described. The processing in steps S11 to S14 is the same as in the first embodiment, therefore, a description thereof is omitted.

The determination function 87d determines whether or not the preset-history information management table contains correction information corresponding to the preset candidate (step S15). After the determination function 87d determines that the preset-history information management table contains correction information corresponding to the preset candidate (YES in step S15), the information management function 87c corrects the preset candidate using the correction information (step S16).

As an example, assume that the preset candidate selected in step S13 be the preset with management No. 1 representing "midesophagus commissural image (two chamber view: 60 to 90 degrees)" and "midesophagus aortic valve long axis image (three chamber view: 100 to 160 degrees)" in the preset-information management table of FIG. 9. In this case, the determination function 87d refers to, for example, preset-history information indicating a status similar to the status "clip approaching the valve" of the preset candidate in the preset-history information management table, to determine whether there is any correction information. After finding correction information, the information management function 87c corrects the preset candidate according to the correction information. If finding no correction information, the information management function 87c does not correct the preset candidate.

As another example, assume that the preset candidate selected in step S13 be the preset with management No. 50 representing "3D image display" in the preset-information management table of the FIG. 9. In this case, the determination function 87d refers to, for example, preset-history information indicating a status similar to the status "clip angle adjustment" of the preset candidate in the preset-history information management table, to determine whether there is any correction information. After finding correction information, the information management function 87c corrects the preset candidate according to the correction information. If finding no correction information, the information management function 87c does not correct the preset candidate.

As another example, assume that the preset candidate selected in step S13 be the preset with management No. 100 that "propose for changing alert condition to set clip attachment mode" in the preset-information management table of FIG. 9. In this case, the determination function 87d refers to, for example, preset-history information indicating a status similar to the status "clip attachment" of the preset candidate in the preset-history information management table, to determine whether there is any correction information. After finding correction information, the information management function 87c corrects the preset candidate on the basis of the correction information. If finding no correction information, the information management function 87c does not correct the preset candidate.

Meanwhile, when the determination function 37d determines that there is no correction information associated with the preset candidate (NO in step S15), the flow proceeds to step S17.

The control function 87a causes the display 83 to present or display, as a proposed preset, the preset candidate corrected using the correction information in step S16 or the preset candidate determined in step S14 if no correction information is found (step S17). Additionally, the control function 87a outputs the details of the proposed preset in the form of audio data from the speaker, when appropriate. The control function 87a further causes the display 83 to present an inquiry as to execution or non-execution of the proposed preset together with the proposed preset. With two or more preset candidates found, the processing in steps S14 to S17 can be performed to each of the preset candidates to display the two or more proposed presets on the display 83.

Subsequently, the control function 87a determines whether or not a proposed preset has been selected (i.e., whether to have received an instruction for executing a proposed preset) (step S18). In response to receipt of an instruction for executing a proposed preset through the input interface circuit 33 (YES in step S18), the control function 37a performs a control in accordance with the proposed preset (step S19). For example, when the proposed preset indicates "3D image display", the control function 37a controls the ultrasound transmitter circuit 71, the ultrasound receiver circuit 73, the B-mode processing circuit 75, the doppler processing circuit 77, the image generator circuit 79, and the display 83 so as to change the settings for "midesophagus commissural image (two chamber view: 60 to 90 degrees)" and "midesophagus aortic valve long axis image (three chamber view: 100 to 160 degrees)" to the settings for "3D image display". For another example, when the proposed preset indicates "propose for changing alert condition to set clip attachment mode", the control function 37a transmits a control signal to the vital signs monitor 43 for instructing the vital signs monitor 43 to change the alert condition to set the clip attachment mode.

Meanwhile, without input of an instruction for executing the proposed preset through the input interface circuit 33 (NO in step S18), the processing in steps S11 to S18 is repeated.

As described above, the ultrasound diagnosis apparatus 100 as the medical image diagnosis apparatus of the present embodiment can attain similar or same effects as the X-ray diagnosis apparatus 1 of the first embodiment.

In particular, the ultrasound diagnosis apparatus 100 of the present embodiment is capable of deciding, according to the status of the current therapeutic procedure, a preset of the settings of the external device that the physician is currently using or will use later in the current therapeutic procedure, to present the preset to the physician as a proposed preset. This makes it possible for the physician to easily and quickly set not only the ultrasound diagnosis apparatus 100 but also the external device currently used or to be used later by selecting the proposed preset.

As a result, the ultrasound diagnosis apparatus 10 of the present embodiment can lessen the physician's burden of implementing desired settings of the ultrasound diagnosis apparatus 100 and the external device used concurrently with the ultrasound diagnosis apparatus 100, and help the physician concentrate on his or her own manipulation.

First Modification

The first and second embodiment have described the example that the X-ray diagnosis apparatus 1 and the ultrasound diagnosis apparatus 100 serving as medical image diagnosis apparatuses perform the therapeutic procedure assist process. Alternatively, a medical image processing apparatus such as a medical workstation may perform the therapeutic procedure assist process as above. Such a medical image processing apparatus is applicable in any environment as long as it can communicate with the medical image diagnosis apparatus such as the X-ray diagnosis apparatus 1 in real time via a network such as an in-hospital network or a cloud network, for example.

Second Modification

The first and second embodiment have described the example that the X-ray diagnosis apparatus 1 and the ultrasound diagnosis apparatus 100 perform the therapeutic procedure assist process. Alternatively, any medical image diagnosis apparatus for use in therapeutic procedures is adoptable, in addition to the X-ray diagnosis apparatus 1 and the ultrasound diagnosis apparatus 100. Examples of the medical image diagnosis apparatus for use in therapeutic procedures include an endoscopic system, an X-ray computer tomography imaging apparatus, and a magnetic resonance imaging apparatus other than the X-ray diagnosis apparatus and the ultrasound diagnosis apparatus.

Third Modification

The second embodiment has described the example that the ultrasound diagnosis apparatus 100 gives a control instruction to the vital signs monitor 43 being an external device, in accordance with the proposed preset acquired through the therapeutic procedure assist process. However, the external device is not limited to the vital signs monitor 43 and may be a contrast injector or another medical image diagnosis apparatus, for example.

In the mitral valve clipping as above, for example, the physician may perform an observation using the X-ray diagnosis apparatus 1 and the ultrasound diagnosis apparatus 100. In this case, for example, the X-ray diagnosis apparatus 1 can give a control instruction to the ultrasound diagnosis apparatus 100 being an external device, or vice versa, in accordance with the proposed preset acquired through therapeutic procedure assist process, thereby implementing the therapeutic procedure assist process in cooperation with each other.

According to at least one of the above embodiments, it is made possible to reduce the burden on the physician in using the preset function of the medical image diagnosis apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus for monitoring a subject in a therapeutic procedure, the apparatus comprising:
   an imaging system configured to perform an imaging process from outside the subject during the therapeutic procedure; and
   processing circuitry configured to:
      determine a status of a current therapeutic procedure;
      determine at least one proposed preset of settings of the medical image diagnosis apparatus, based on the determined status of the current therapeutic procedure; and
      perform control in accordance with the determined at least one proposed preset,
   wherein the processing circuitry is further configured to
      manage a plurality of sets of preset-history information, each of the sets of preset-history information representing a preset of the medical image diagnosis apparatus used in the current therapeutic procedure and the status of the current therapeutic procedure when the preset is used, in association with each other; and
      determine the at least one proposed preset with reference to a plurality of sets of preset information, the plurality of sets of preset-history information, and a proposed-preset determination rule, each of the sets of preset information representing a preset of the settings of the medical image diagnosis apparatus and a status of a therapeutic procedure in association with each other, the proposed-preset determination rule representing a criterion for determining the proposed preset.

2. The medical image diagnosis apparatus according to claim 1, wherein the processing circuitry is further configured to determine the status of the current therapeutic procedure from a medical image acquired by the imaging system.

3. The medical image diagnosis apparatus according to claim 2, wherein the processing circuitry is further configured to determine the status of the current therapeutic procedure from a location of a first object included in the acquired medical image.

4. The medical image diagnosis apparatus according to claim 3, wherein the processing circuitry is further configured to determine the status of the current therapeutic procedure from a location of the first object with respect to a second object included in the acquired medical image.

5. The medical image diagnosis apparatus according to claim 4, wherein the first object is a device inserted into the subject.

6. The medical image diagnosis apparatus according to claim 1, wherein the processing circuitry is further configured to determine the status of the current therapeutic procedure from at least one of:
   an image of an operating room in which the medical image diagnosis apparatus is installed, or
   audio data acquired in the operating room.

7. The medical image diagnosis apparatus according to claim 1, wherein the at least one proposed preset includes a setting of at least one of:
   a location of an imaging device of the medical image diagnosis apparatus,
   an imaging method,
   a position of a display of the medical image diagnosis apparatus, or
   a display layout of the display the medical image diagnosis apparatus.

8. The medical image diagnosis apparatus according to claim 1, wherein the at least one proposed preset includes a setting of an external device communicable with the medical image diagnosis apparatus.

9. The medical image diagnosis apparatus according to claim 8, wherein the external device is any of a vital signs monitor, a contrast injector, and another medical image diagnosis apparatus.

10. A medical image diagnosis apparatus for monitoring a subject in a therapeutic procedure, the apparatus comprising:
    processing circuitry configured to
       determine a status of a current therapeutic procedure;
       determine at least one proposed preset of settings of the medical image diagnosis apparatus based on the determined status of the current therapeutic procedure; and
       perform control in accordance with the determined at least one proposed preset,
    wherein the processing circuitry is further configured to:
       manage a plurality of sets of preset-history information, each of the sets of preset-history information representing a preset of the medical image diagnosis apparatus used in the current therapeutic procedure and the status of the current therapeutic procedure when the preset is used, in association with each other, and
       determine the at least one proposed preset with reference to a plurality of sets of preset information, the plurality of sets of preset-history information, and a proposed-preset determination rule, each of the sets of preset information representing a preset of the settings of the medical image diagnosis apparatus and a status of a therapeutic procedure in association with each other, the proposed-preset determination rule representing a criterion for determining the proposed preset.

11. The medical image diagnosis apparatus according to claim 10, wherein the processing circuitry is further configured to:
    manage the plurality of sets of preset-history information for each user, and
    determine the at least one proposed preset with reference to the plurality of sets of preset-history information of the user.

12. The medical image diagnosis apparatus according to claim 11, wherein the plurality of sets of preset-history information includes correction information with respect to a preset of the medical image diagnosis apparatus used in the current therapeutic procedure, and the processing circuitry is further configured to determine the at least one proposed preset with reference to the correction information.

13. A medical information processing apparatus for use monitoring a subject in a therapeutic procedure on a subject, the apparatus comprising:

processing circuitry configured to:
determine a status of a current therapeutic procedure;
determine at least one proposed preset of settings of the medical image diagnosis apparatus based on the determined status of the current therapeutic procedure, the medical image diagnosis apparatus including an imaging system configured to perform an imaging process from outside the subject during the therapeutic procedure; and
perform control in accordance with the determined at least one proposed preset;
manage a plurality of sets of preset-history information, each of the sets of preset-history information representing a preset of a medical image diagnosis apparatus used in the current therapeutic procedure and the status of the current therapeutic procedure when the preset is used, in association with each other; and
decide the at least one proposed preset with reference to a plurality of sets of preset information, the plurality of sets of preset-history information, and a proposed-preset determination rule, each of the sets of preset information representing a preset of the settings of the medical image diagnosis apparatus and a status of a therapeutic procedure in association with each other, the proposed-preset determination rule representing a criterion for determining the proposed preset.

14. A medical information processing method for monitoring a subject in a therapeutic procedure on a subject, the method comprising:

determining a status of a current therapeutic procedure;
determining at least one proposed preset of settings of a medical image diagnosis apparatus based on the determined status of the current therapeutic procedure, the medical image diagnosis apparatus including an imaging system configured to perform an imaging process from outside the subject during the therapeutic procedure;
performing control in accordance with the determining at least one proposed preset
managing a plurality of sets of preset-history information, each of the sets of preset-history information representing a preset of a medical image diagnosis apparatus used in the current therapeutic procedure and the status of the current therapeutic procedure when the preset is used, in association with each other; and
deciding the at least one proposed preset with reference to a plurality of sets of preset information, the plurality of sets of preset-history information, and a proposed-preset determination rule, each of the sets of preset information representing a preset of the settings of the medical image diagnosis apparatus and a status of a therapeutic procedure in association with each other, the proposed-preset determination rule representing a criterion for determining the proposed preset.

15. The medical information processing method according to claim 14, wherein the step of determining the status further comprises determining the status of the current therapeutic procedure from a medical image acquired by the imaging system.

16. The medical information processing method according to claim 15, wherein the step of determining the status further comprises determining the status of the current therapeutic procedure from a location of a first object included in the acquired medical image.

17. The medical information processing method according to claim 16, wherein the step of determining the status further comprises determining the status of the current therapeutic procedure from a location of the first object with respect to a second object included in the acquired medical image.

18. The medical information processing method according to claim 14, wherein the step of determining the status further comprises determining the status of the current therapeutic procedure from at least one of:
an image of an operating room in which the medical image diagnosis apparatus is installed, or
audio data acquired in the operating room.

19. The medical information processing method according to claim 14, wherein the at least one proposed preset includes a setting of at least one of:
a location of an imaging device of a medical image diagnosis apparatus,
an imaging method,
a position of a display of the medical image diagnosis apparatus, or
a display layout of the display of the medical image diagnosis apparatus.

* * * * *